(12) United States Patent
Koumura et al.

(10) Patent No.: US 7,973,172 B2
(45) Date of Patent: Jul. 5, 2011

(54) ORGANIC COMPOUND, SEMICONDUCTOR FILM ELECTRODE EMPLOYING THE ORGANIC COMPOUND, PHOTOELECTRIC CONVERSION ELEMENT EMPLOYING THE ORGANIC COMPOUND, AND PHOTOELECTROCHEMICAL SOLAR CELL EMPLOYING THE ORGANIC COMPOUND

(75) Inventors: Nagatoshi Koumura, Tsukuba (JP); Koujirou Hara, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 291 days.

(21) Appl. No.: 12/294,919

(22) PCT Filed: Mar. 27, 2007

(86) PCT No.: PCT/JP2007/056383
§ 371 (c)(1),
(2), (4) Date: Sep. 26, 2008

(87) PCT Pub. No.: WO2007/119525
PCT Pub. Date: Oct. 25, 2007

(65) Prior Publication Data
US 2010/0174095 A1 Jul. 8, 2010

(30) Foreign Application Priority Data
Mar. 31, 2006 (JP) .................................. 2006-100920

(51) Int. Cl.
*C07D 209/82* (2006.01)
*C07D 409/14* (2006.01)
(52) U.S. Cl. .......................................... 548/440; 549/59
(58) Field of Classification Search ................... 548/440
See application file for complete search history.

(56) References Cited

U.S. PATENT DOCUMENTS
4,927,721 A 5/1990 Gratzel et al.
5,084,365 A 1/1992 Gratzel et al.

FOREIGN PATENT DOCUMENTS
JP 2004-095450 3/2004
JP 2004-207224 7/2004
JP 2004207224 A * 7/2004
JP 2004-292744 10/2004

OTHER PUBLICATIONS

STN_12294919B_preliminary_09102010.*
Koumura et al., Journal of American Chemical Society, 2006, vol. 128, p. 14256-57.*
Bach, U. et al. (Oct. 8, 1998). "Solid-State Dye-Sensitized Mesoporous TiO₂ Solar Cells with High Proton-to-Electron Conversion Efficiencies," *Nature* 395:583-585.
Barbé, C. J. et al. (1997). "Nanocrystalline Titanium Oxide Electrodes for Photovoltaic Applications," *Journal of the American Ceramic Society* 80(12):3157-3171.
Hara, K. et al. (2000). "Highly Efficient Photon-to-Electron Conversion with Mercurochrome-Sensitized Nanoporous Oxide Semiconductor Solar Cells," *Solar Energy Materials & Solar Cells* 64:115-134.
Hara, K. et al. (2005). "Electron Transport in Coumarin-Dye-Sensitized Nanocrystalline TiO₂ Electrodes," *The Journal of Physical Chemistry B* 109:23776-23778.
Hara, K. et al. (2005). "Oligothiophene-Containing Coumarin Dyes for Efficient Dye-Sensitized Solar Cells," *The Journal of Physical Chemistry B* 109:15476-15482.
International Search Report mailed May 1, 2007, for PCT Application No. PCT/JP2007/056383 filed Mar. 27, 2007, 4 pages.
Koumura, N. et al. (2006). "Alkyl-Functionalized Organic Dyes for Efficient Dye-Sensitized Solar Cells," 16th International Conference on Photochemical Convension and Storage of Solar Energy (IPS-16), Uppsala, Sweden, Abstract, 1 page.
Koumura, N. et al. (2006). "Alkyl-Functionalized Organize Dyes for Efficient Molecular Photovoltaics," *Journal of the American Chemical Society* 128:14256-14257.
Koumura, N. et al. (Jul. 24, 2008). "Hexylthiophene-Functionalized Carbazole Dyes for Efficient Molecular Photovolatics," The 8th International Symposium on Function π-Electron Systems (F π-8), Graz, Austria, Abstract, 1 page.
Kubo, W. et al. (2002). "Quasi-Solid-State Dye Sensitized Solar Cells Using Room Temperature Molten Salts and Low-Molecular Weight Gelator," *Chemical Communications*, pp. 374-375.

(Continued)

*Primary Examiner* — Yong Chu
(74) *Attorney, Agent, or Firm* — Morrison & Foerster LLP

(57) ABSTRACT

The present invention provides: an organic compound increasing an open circuit voltage, and showing high photoelectric conversion efficiency; a semiconductor film electrode employing the organic compound as a dye; a photoelectric conversion element employing the semiconductor film electrode; and a photoelectrochemical solar cell employing the photoelectric conversion element. The organic compound is represented by the following general formula:

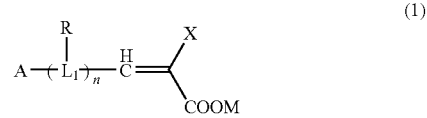

(1)

wherein A is a carbazole ring; $L_1$ is an electron transfer linking group having at least one heterocyclic ring selected from the group consisting of a thiophene ring, a furan ring, a pyrrole ring, and a condensed heterocyclic ring formed from any combinations of these rings; R is a substituent group bound to at least one electron transfer linking group selected from the group consisting of an alkyl group, an alkoxy group, and an aryl group; X is at least one electron withdrawing group selected from the group consisting of a cyano group, a carboxylic acid group, an ester group, an amide group, a trifluoromethyl group, a pentafluoroethyl group, a sulfonate group, and a trifluoromethanesulfonate group; M is a hydrogen atom or a salt-forming cation; and n is an integer of 1 to 12.

4 Claims, 1 Drawing Sheet

OTHER PUBLICATIONS

Kubo, W. et al. (2003). "Photocurrent-Determining Processes in Quasi-Solid-State Dye-Sensitized Solar Cells Using Ionic Gel Electrolytes," *The Journal of Physical Chemistry B* 107:4374-4381.

Murakoshi, K. et al. (1998). "Fabrication of Solid-State Dye-Sensitized $TiO_2$ Solar Cells Combined with Polypyrrole," *Solar Energy Materials and Solar Cells* 55:113-125.

Nakade, S. et al. (2005). "Role of Electrolytes on Charge Recombination in Dye-Sensitized $TiO_2$ Solar Cell (1): The Case of Solar Cells Using the $I^-/I_3^-$ Redox Couple," *The Journal of Physical Chemistry B* 109:3480-3487.

Nazeeruddin, M. K. et al. (1993). "Conversion of Light to Electricity by cis-$X_2$Bis(2,2'-Bipyridyl-4,4'-Dicarboxylate)Ruthenium(II) Charge-Transfer Sensitizers (X=CL$^-$, Br$^-$, I$^-$, CN$^-$, and SCN$^-$) on Nanocrystalline TiO2 Electrodes," *Journal of the American Chemical Society* 115:6382-6390.

O'Regan, B. et al. (Oct. 24, 1991). "A Low-Cost High-Efficiency Solar Cell Based on Dye-Sensitized Colloidal $TiO_2$ Films," *Nature* 353:737-740.

Sayama, K. et al. (2001). "Significant Effects of the Distance Between the Cyanine Dye Skeleton and the Semiconductor Surface on the Photoelectrochemical Properties of Dye-Sensitized Porous Semiconductor Electrodes," *New Journal of Chemistry* 25:200-202.

Tennakone, K. et al. (1998). "Sensitization of Nano-Porous Films $TiO_2$ with Santalin (Red Sandalwood Pigment) and Construction of Dye-Sensitized Solid-State Photovoltaic Cells," *Journal of Photochemistry and Photobiology A: Chemistry* 117:137-142.

Koumura, N. et al. (2006). "Alkyl-Functionalized Organic Dyes for Efficient Molecular Photovoltaics," *Journal of the American Chemical Society* 128:14256-14257.

Koumura, N. et al. (Jul. 12, 2008). "Hexylthiophene-Functionalized Carbazole Dyes for Efficient Molecular Photovolatics," The 8th International Symposium on Function π-Electron Systems (F π-8), Graz, Austria, Abstract, 1 page.

\* cited by examiner

ORGANIC COMPOUND, SEMICONDUCTOR FILM ELECTRODE EMPLOYING THE ORGANIC COMPOUND, PHOTOELECTRIC CONVERSION ELEMENT EMPLOYING THE ORGANIC COMPOUND, AND PHOTOELECTROCHEMICAL SOLAR CELL EMPLOYING THE ORGANIC COMPOUND

CROSS REFERENCE TO RELATED APPLICATIONS

This application is a U.S. National Phase Application of International Application No. PCT/JP2007/056383, filed Mar. 27, 2007, which claims priority to Japan Patent Application No. JP-100920/2006, filed Mar. 31, 2006, the contents of which are hereby incorporated by reference into the present disclosure in their entirety.

TECHNICAL FIELD

The present invention relates to: an organic dye; a semiconductor film electrode employing the organic dye as a photosensitizer; a photoelectric conversion element employing the organic dye as a photosensitizer; and a photoelectrochemical solar cell employing the photoelectric conversion element.

BACKGROUND ART

In 1993, Professor Graetzel et al. at Ecole Polytechnique Fédérale de Lausanne, Switzerland, invented a dye-sensitized solar cell (See Patent Document 1 and Non-Patent Document 1 and 2).

The solar cell employs a sensitizer made from a ruthenium complex, and includes: a nanoporous film electrode of an oxide semiconductor having a wide bandgap, such as titanium oxide or zinc oxide in a form of nanoparticle; an iodine redox electrolyte solution; and a counter electrode. The solar cell has been attracting attention as one of next-generation solar cells, and actively researched and developed recently, because it has relatively high photoelectric conversion efficiency (solar energy conversion efficiency of 7% to 10%), and low-cost production potential.

The dye-sensitized solar cell invented by Graetzel et al. employs a complex as a photosensitizer, which complex containing ruthenium that is a precious metal. For large-scale electric power generation, the solar cell needs a lot of a ruthenium complex, so that it has been pointed out that the solar cell has a resource limitation problem.

With such a background, a dye-sensitized solar cell employing an organic dye as a photosensitizer, which organic dye contains no precious metals such as ruthenium, has been also researched and developed.

Examples of the organic dye that has been applied to the solar cell encompass: a phenylxanthene dye, a phthalocyanine dye, a cyanine dye, a merocyanine dye, a porphyrin dye, and an azo dye (See Non-Patent Documents 3 and 4). Particularly, a coumarin dye (See Non-Patent Document 5) is almost the same as the ruthenium complex in absorption wavelength range, and showed high photoelectric conversion efficiency. However, there has been a problem that the dye-sensitized solar cell employing the organic dye generally has a lower open circuit voltage and conversion efficiency than the solar cell employing the ruthenium complex.

For example, it has been known that the dye-sensitized solar cell employing the coumarin dye is lower than the solar cell employing the ruthenium complex in open circuit voltage because in a case of coumarin dye, the electrons spreading in titanium oxide have a shorter life time due to recombination than in a case of the ruthenium complex (See Non-Patent Document 6).

Development of the dye-sensitized solar cell, and use of the organic dye in the development are valuable in consideration of the future, and it has been imperative to research and develop the solar cell that has a lower open circuit voltage and higher conversion efficiency.

(Patent Document 1)
Japanese Patent No. 2664194 Specification
(Non-Patent Document 1)
Nature, 353, 737 (1991)
(Non-Patent Document 2)
J. Am. Chem. Soc., 115, 6382 (1993)
(Non-Patent Document 3)
Sol. Energy Mater. Sol. Cells, 64, 115 (2000)
(Non-Patent Document 4)
New J. Chem., 25, 200 (2001)
(Non-Patent Document 5)
J. Phys. Chem. B, 109, 15476 (2005)
(Non-Patent Document 6)
J. Phys. Chem. B, 109, 23776 (2005)

DISCLOSURE OF INVENTION

Problem to be Solved by the Invention

An object of the present invention is to provide: an organic compound increasing an open circuit voltage and showing high photoelectric conversion efficiency; a semiconductor film electrode employing the organic compound as a dye; a photoelectric conversion element employing the semiconductor film electrode; and a dye-sensitized solar cell employing the photoelectric conversion element.

Means for Solving Problem

In view of the object described above, as a result of diligent study, the inventors of the present invention found that an unique organic compound described below is suitable for use as an organic dye of a semiconductor film electrode, and the object can be attained by constituting a photoelectric conversion element employing the electrode and a high-performance photoelectrochemical solar cell employing the element. Based on the finding, the inventors of the present invention accomplished the present invention.

That is, the present application provides the following inventions.

(1) An organic compound represented by the following general formula (1):

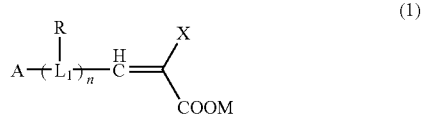

(1)

wherein A is a carbazole ring; $L_1$ is an electron transfer linking group having at least one heterocyclic ring selected from the group consisting of a thiophene ring, a furan ring, a pyrrole ring, and a condensed heterocyclic ring formed from any combinations of these rings; R is a substituent group bound to at least one electron transfer linking group selected from the group consisting of an alkyl group, an alkoxy group, and an aryl group; X is at least one electron withdrawing group selected from the group consisting of a cyano group, a carboxylic acid group, an ester group, an amide group, a trifluoromethyl group, a pentafluoroethyl group, a sulfonate group, and a trifluoromethanesulfonic group; M is a hydrogen atom or a salt-forming cation; and n is an integer of 1 to 12.

(2) A semiconductor film electrode employing the organic compound according to (1) as an organic dye.

(3) A photoelectric conversion element employing the semiconductor film electrode according to (2).

(4) A photoelectrochemical solar cell employing the photoelectric conversion element according to (3).

EFFECT OF THE INVENTION

By employing an organic compound of the present invention in a photoelectric conversion element as an organic dye, it becomes possible to improve photoelectric conversion efficiency compared with a case of employing a conventional organic dye. Specifically, a steric hindrance effect of R suppresses a recombination process, so that it becomes possible to significantly raise an open circuit voltage that has been considered impossible to be raised anymore with a conventional organic dye. As a result, it becomes possible to significantly improve performance of the photoelectrochemical solar cell made of the photoelectric conversion element.

EXPLANATION OF NUMERALS

Figure 1:
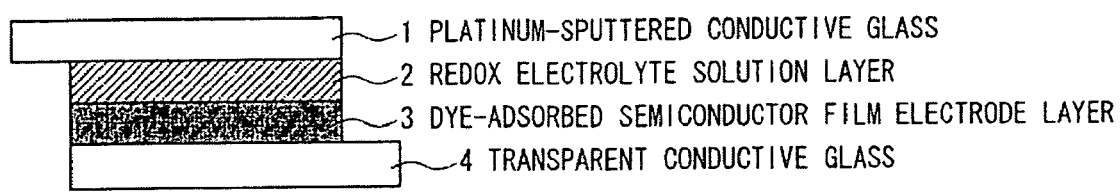
FIG. 1 illustrates an example of a block diagram of a photoelectrochemical solar cell used in Example of the present invention.

1. PLATINUM-SPUTTERED CONDUCTIVE GLASS
2. REDOX ELECTROLYTE SOLUTION LAYER
3. DYE-ADSORBED SEMICONDUCTOR FILM ELECTRODE LAYER
4. TRANSPARENT CONDUCTIVE GLASS

BEST MODE FOR CARRYING OUT THE INVENTION

An organic compound according to the present invention is represented by the following general formula (1):

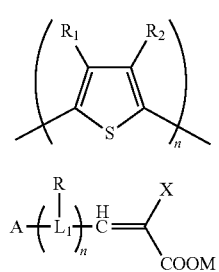

(1)

wherein A is a carbazole ring; $L_1$ is an electron transfer linking group having at least one heterocyclic ring selected from the group consisting of a thiophene ring, a furan ring, a pyrrole ring, and a condensed heterocyclic ring formed from any combinations of these rings; R is a substituent group bound to at least one electron transfer linking group selected from the group consisting of an alkyl group, an alkoxy group, and an aryl group; X is at least one electron-withdrawing group selected from the group consisting of a cyano group, a carboxylic acid group, an ester group, an amide group, a trifluoromethyl group, a pentafluoroethyl group, a sulfonate group, and a trifluoromethanesulfonic group; M is a hydrogen atom or a salt-forming cation; and n is an integer of 1 to 12.

The carbazole ring A may have a substituent group such as an alkyl group, on a carbon ring or a nitrogen atom, or may be condensed with a carbon ring, such as a benzene ring or a naphthalene ring.

Examples of the substituent group encompass: straight $C_{1-20}$ (preferably $C_{1-12}$) alkyl groups such as a methyl group, and a hexyl group; branched $C_{1-20}$ (preferably $C_{1-12}$) alkyl groups such as an isobutyl group, and a 2-ethyloctyl group; $C_{1-20}$ (preferably $C_{1-12}$) alkoxy groups such as a methoxy group, and a butoxy group; $C_{3-20}$ (preferably $C_{5-12}$) aryl groups such as a phenyl group, and a naphthyl group; monoalkylamino groups having a $C_{1-20}$ (preferably $C_{1-12}$) alkyl group such as a methylamino group, and an octylamino group; dialkylamino groups having a $C_{1-20}$ (preferably $C_{1-12}$) alkyl group such as a diethylamino group; cyclic amino groups having a 5 to 8-membered (preferably 5 to 6-membered) ring, such as a piperidyl group; halogen groups such as a chloro group, a bromo group, and an iodine group; a hydroxyl group; a nitro group; and an amino group.

In the general formula (1), $L_1$ is an electron transfer linking group having at least one heterocyclic ring selected from the group consisting of a thiophene ring, a furan ring, a pyrrole ring, and a condensed heterocyclic ring formed from any combinations of these rings.

Examples of such an electron transfer linking group are described below.

(1) A Linking Group Having a Thiophene Ring

This linking group may be a group represented by the following general formula (2):

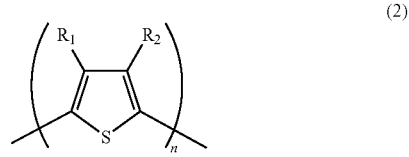

(2)

wherein n is an integer of 1 to 12, preferably 1 to 8, and $R_1$ and $R_2$ are a hydrogen atom or a substituent group, but at least one of them should be the substituent group. Examples of such a substituent group encompass: straight $C_{1-20}$ (preferably $C_{1-12}$) alkyl groups such as a methyl group, and a hexyl group; branched $C_{1-20}$ (preferably $C_{1-12}$) alkyl groups such as an isobutyl group, and a 2-ethyloctyl group; $C_{1-20}$ (preferably $C_{1-12}$) alkoxy groups such as a methoxy group, and a butoxy group; $C_{3-20}$ (preferably $C_{5-12}$) aryl groups such as a phenyl group, and a naphthyl group; monoalkylamino groups having a $C_{1-20}$ (preferably $C_{1-12}$) alkyl group such as a methylamino group, and an octylamino group; dialkylamino groups having a $C_{1-20}$ (preferably $C_{1-12}$) alkyl group such as a diethylamino group; cyclic amino groups having a 5 to 8-membered (preferably 5 to 6-membered) ring, such as a piperidyl group; halogen groups such as a chloro group, a bromo group, and an iodine group; a hydroxyl group; a cyano group; a nitro group; and an amino group.

(2) A Linking Group Having a Furan Ring

This linking group may be a group represented by the following general formula (3):

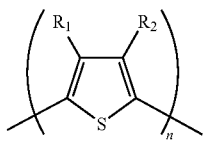

(3)

wherein n, $R_1$, and $R_2$ are the same as described above.

(3) A Linking Group Having a Pyrrole Ring

This linking group may be a group represented by the following general formula (4):

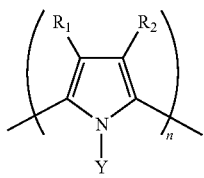

(4)

wherein n, $R_1$, and $R_2$ are the same as described above, and Y is a hydrocarbon group that may have a hydrogen atom or a substituent group. This hydrocarbon group may be an aliphatic hydrocarbon group or an aromatic hydrocarbon group. Examples of the aliphatic hydrocarbon group include: $C_{1-12}$ (preferably $C_{1-8}$) alkyl groups; $C_{3-12}$ (preferably $C_{4-8}$) cycloalkyl groups; $C_{2-12}$ (preferably $C_{2-8}$) alkenyl groups; and $C_{3-12}$ (preferably $C_{4-8}$) cycloalkenyl groups. The aromatic hydrocarbon group has carbon atoms of 6 to 18, preferably 6 to 12. The aromatic hydrocarbon group may be a $C_{6-18}$ (preferably $C_{6-12}$) aryl group or a $C_{7-18}$ (preferably $C_{7-12}$) arylalkyl group.

$L_1$ may be any one of the linking groups described above. However, a thiophene ring that is represented by the general formula (2) may be preferably used in consideration of making a flow of electrons smooth, the flow from the carbazole ring A to a cyanoacetic acid site that is an electron-withdrawing group positioned opposite to the carbazole ring A. Further, a substituent group preferably included in this thiophene ring may be an electronically-inactive group, that is, an organic group not obstructing a flow of electrons of the electron transfer linking group, or, another organic group, like an electron-releasing group, having a steric hindrance effect to push the electrons toward the electron transfer linking group. That is, by the presence of the substituent group having such a steric hindrance effect in the thiophene ring, the steric hindrance effect suppresses a recombination process that is a phenomenon in which an electron put into titanium oxide comes back in an organic dye molecule or an iodine redox in an electrolyte solution, so that it becomes possible to significantly raise an open circuit voltage that has been considered impossible to be raised anymore with a conventional organic dye. As a result, it becomes possible to significantly improve performance of the photoelectrochemical solar cell made of the photoelectric conversion element.

X is at least one electron-withdrawing group selected from the group consisting of: a cyano group; a carboxylic acid group; an ester group; an amide group; a trifluoromethyl group; a pentafluoroethyl group; a sulfonate group; and a trifluoromethanesulfonic group.

M is a hydrogen atom or a salt-forming cation. Examples of this salt-forming cation include: alkali metals, such as lithium, sodium, and potassium; alkali earth metals, such as calcium, and magnesium; a cation that is induced from another metal; an ammonium cation, an organic ammonium cation derived from amine; and the like.

Next, the following shows specific examples of the compound (an organic dye) represented by the general formula (1), but the present invention is not limited to these compounds.

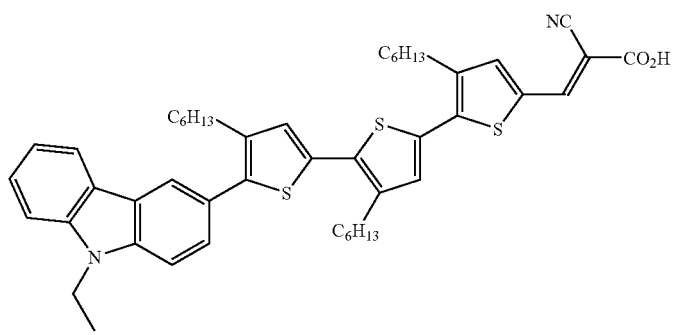

(5)

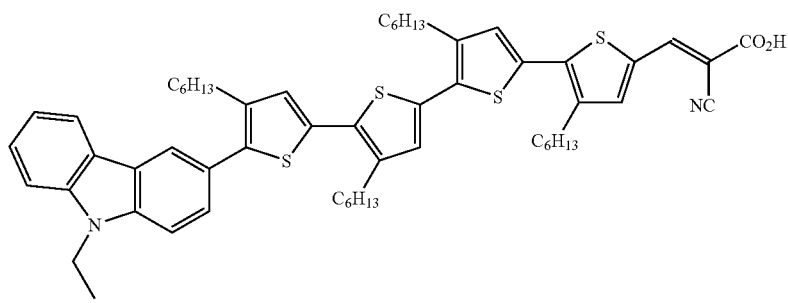

(6)

-continued
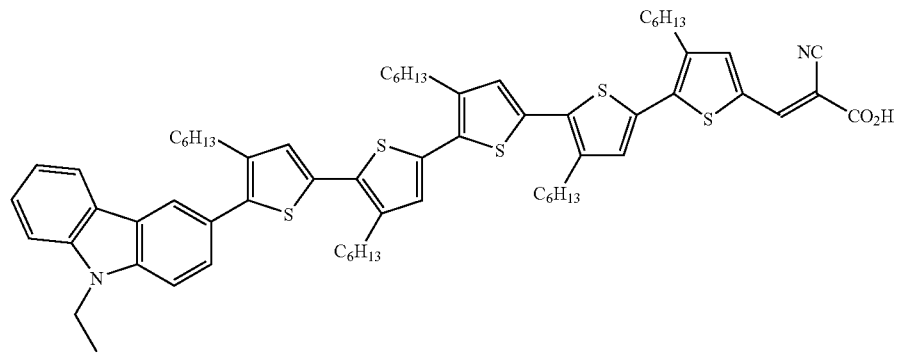
(7)
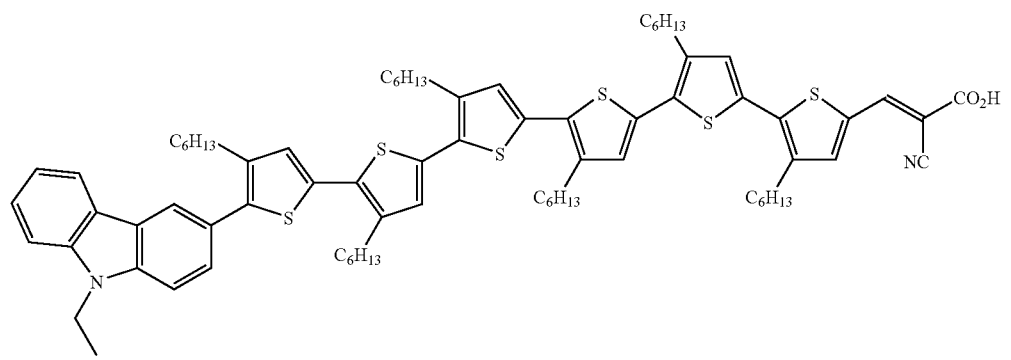
(8)
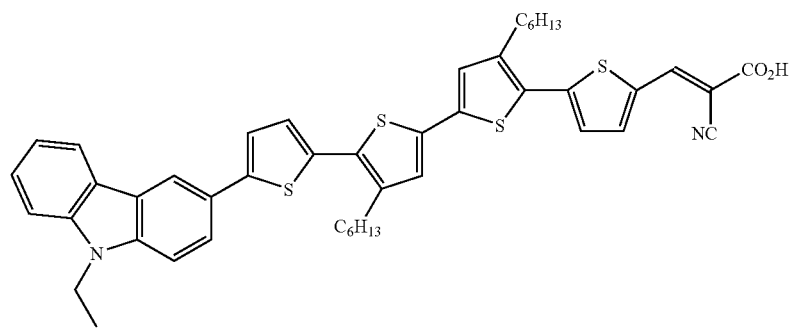
(9)
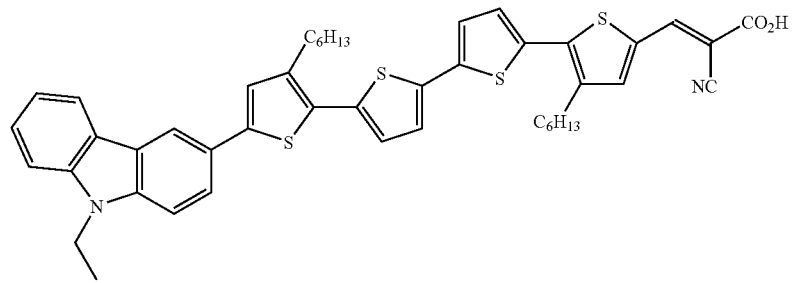
(10)

(11)
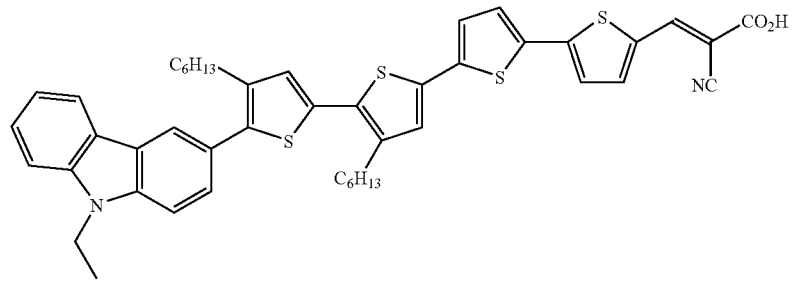
(12)
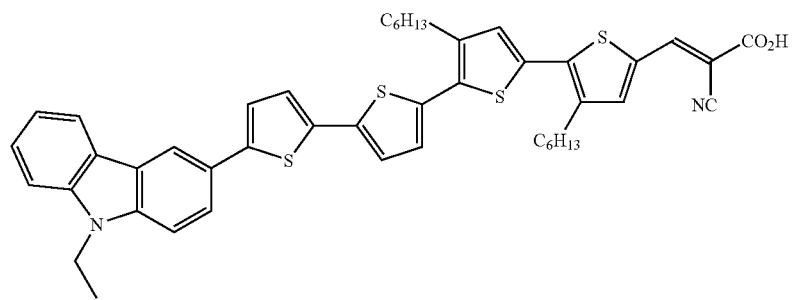
(13)
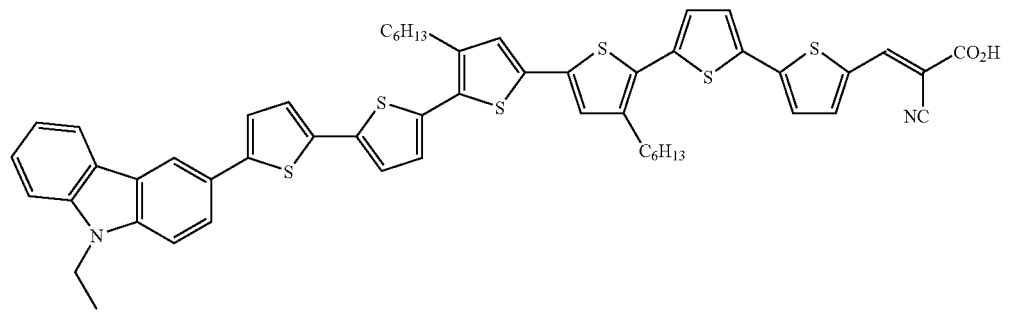
(14)
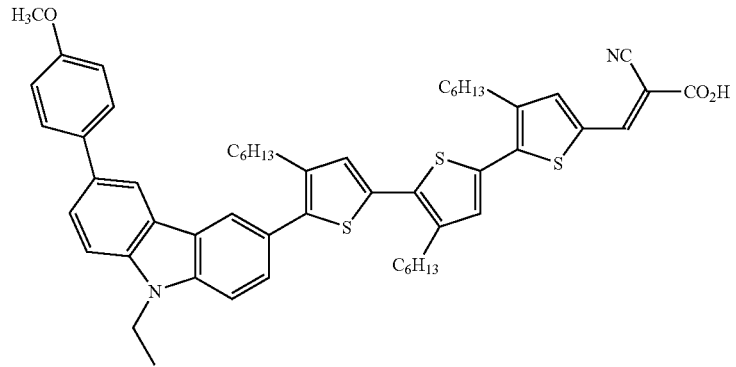

(15)
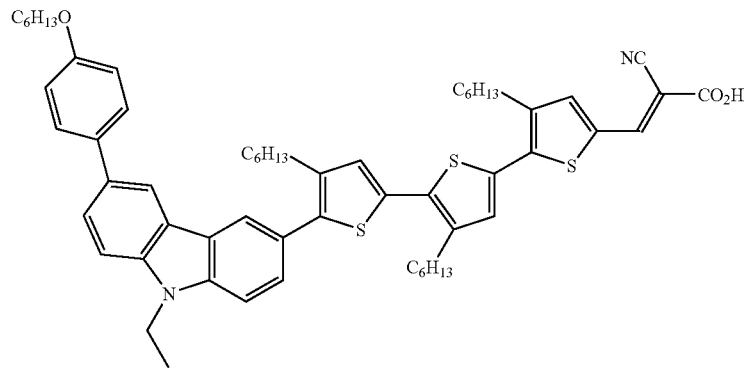
(16)
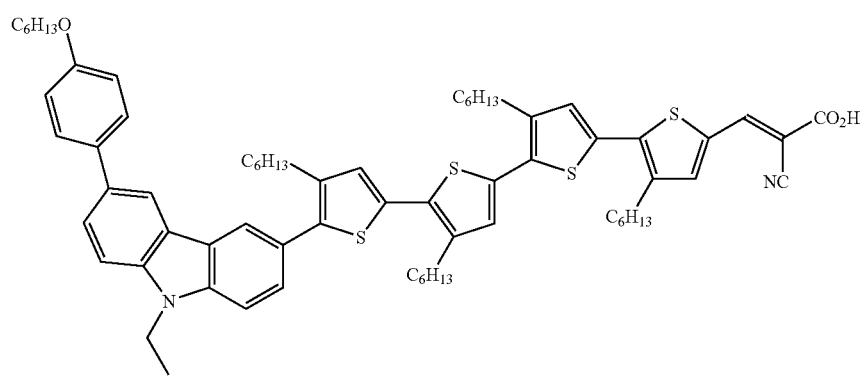
(17)
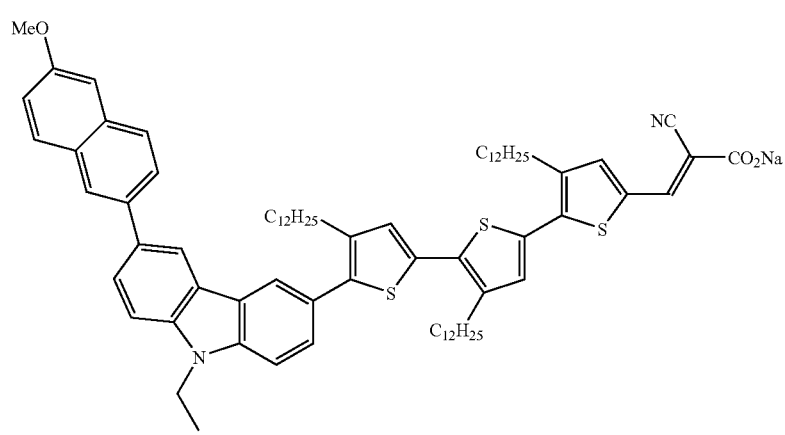
(18)
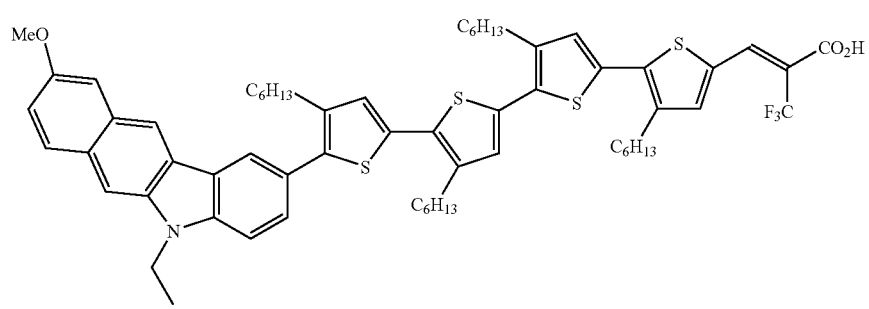

(19)
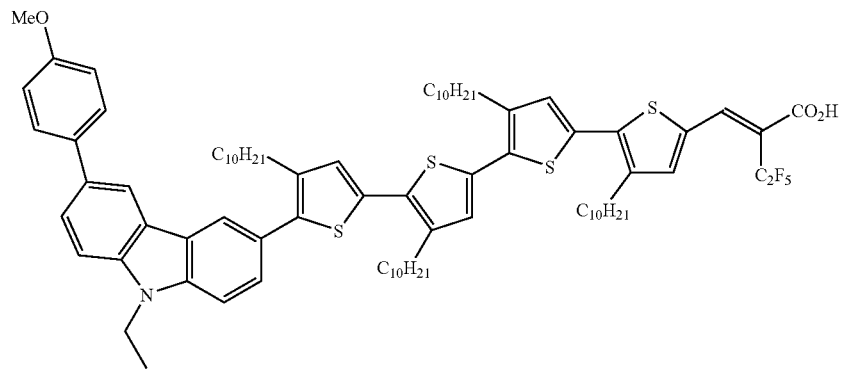
(20)
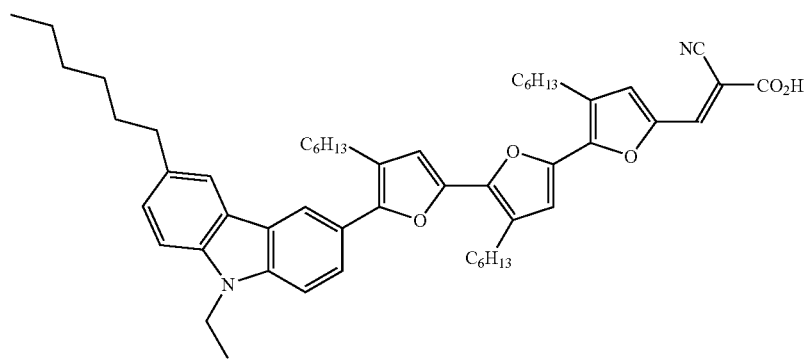
(21)
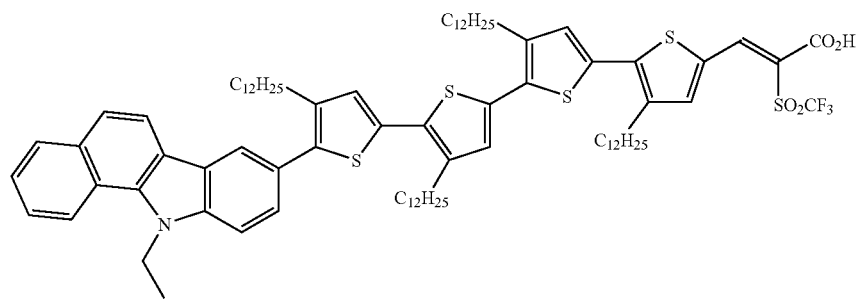
(22)
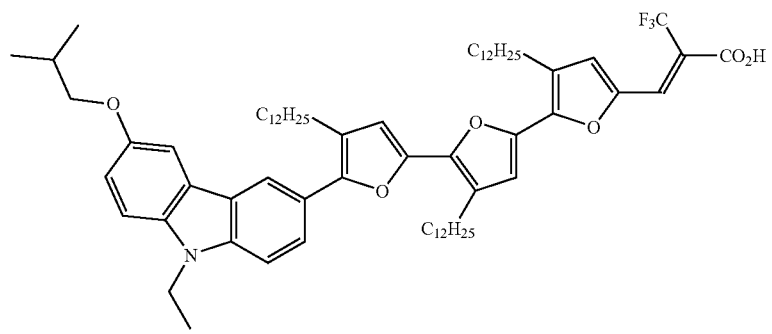

(23)
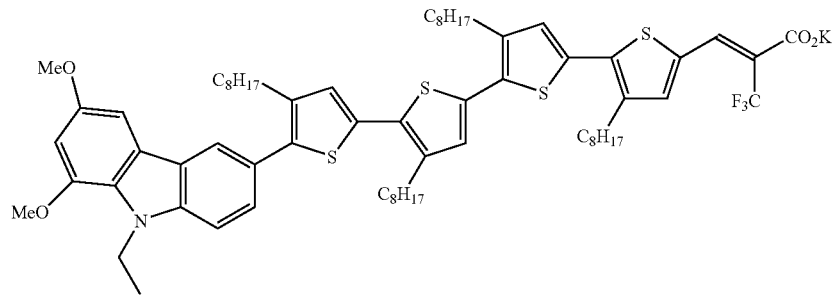
(24)
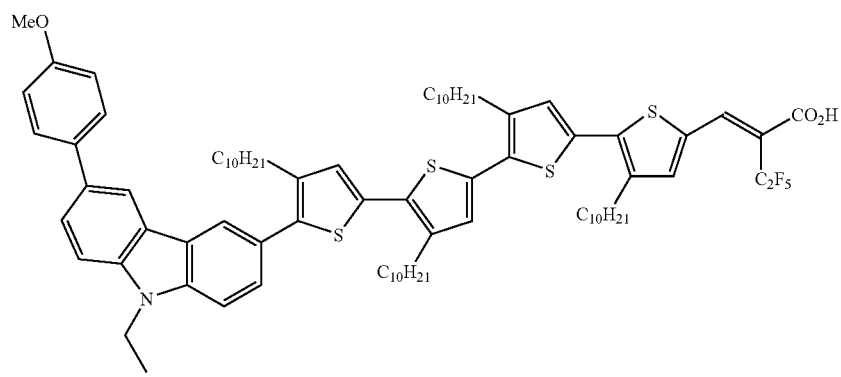
(25)
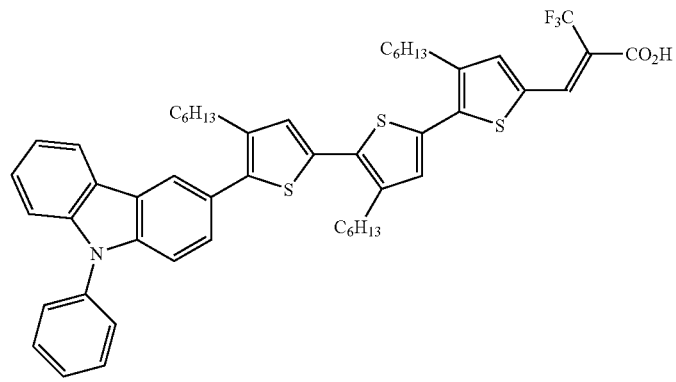
(26)
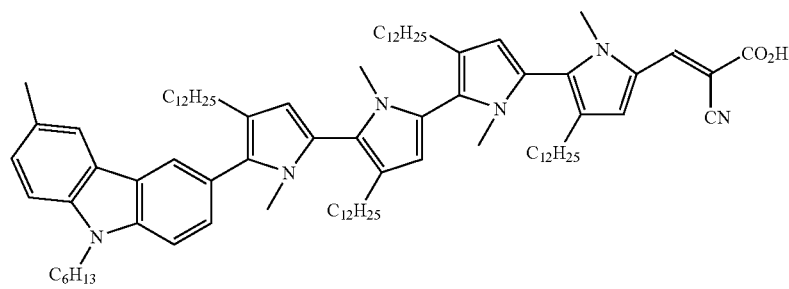

-continued
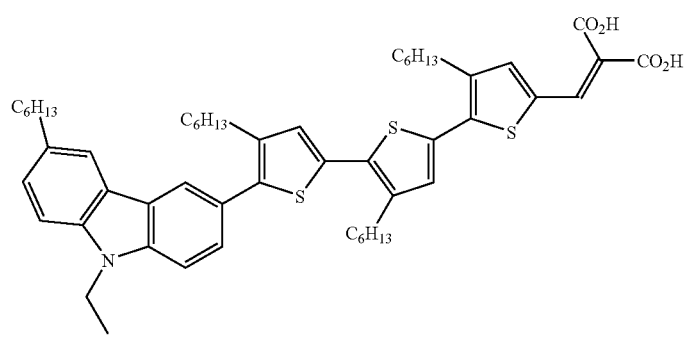
(27)
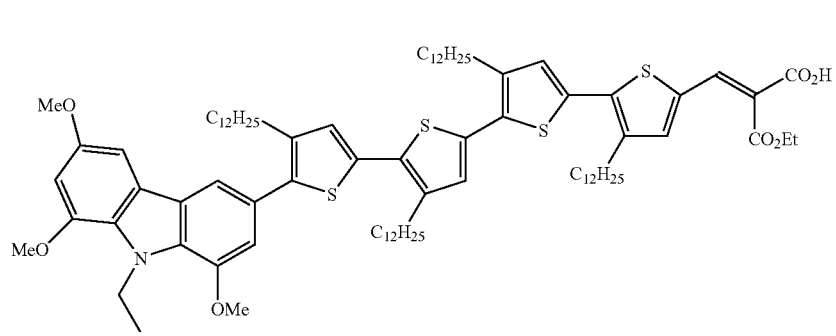
(28)
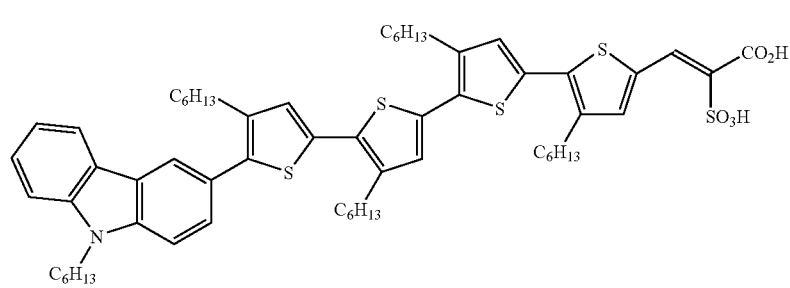
(29)
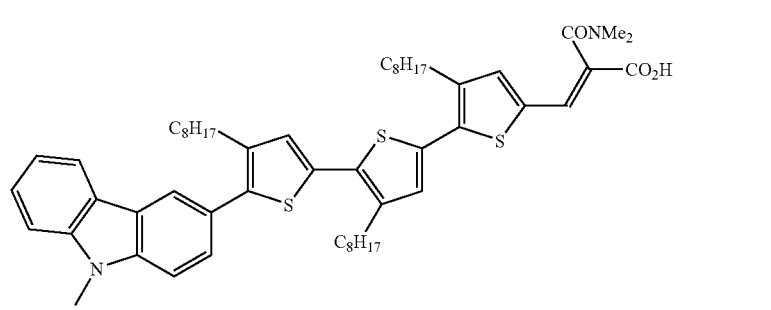
(30)
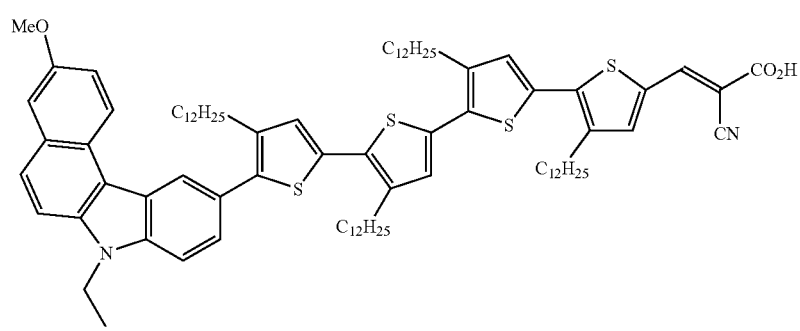
(31)

The compound according to the present invention, represented by the general formula (1), may be synthesized in any way, and may be easily synthesized by a method described below. The synthesis method slightly differs in detail depending on various dye molecules, but is basically a method including three stages. In a first stage, the carbazole ring corresponding to A to which an iodine atom, a bromine atom, and the like, are bound, and a boric acid ester derivative of the electron transfer linking group corresponding to $L_1$ such as a thiophene ring, and a furan ring, are bound to each other by a Suzuki coupling reaction. In a second stage, an intermediate formed by associating A with $L_1$ is treated with a Vilsmeier reagent so that aldehyde is introduced into an opposite side of a side bound to the carbazole ring of the electron transfer linking group $L_1$ such as a thiophene ring and a furan ring. In a third stage, by making this aldehyde derivative and cyanoacetic acid react with each other in the presence of a base such as piperidine, a corresponding organic dye compound can be obtained.

The organic compound according to the present invention, represented by the general formula (1), can improve photoelectric conversion efficiency compared with the conventional organic dyes. Specifically, the steric hindrance effect generated by a substituent group R that is bound to the electron transfer linking group $L_1$ suppresses a recombination process that is the phenomenon in which the electron put into titanium oxide comes back in the organic dye molecule, or an iodine redox in the electrolyte solution, so that it becomes possible to significantly raise the open circuit voltage that has been considered impossible to be raised anymore with the conventional organic dye. As a result, it becomes possible to significantly improve performance of the photoelectrochemical solar cell made of the photoelectric conversion element.

For this reason, the organic compound according to the present invention, represented by the formula (1), can be efficiently used as an organic dye for forming a semiconductor film electrode.

In this case, a substrate of the semiconductor film electrode may be a well-known substrate as it is. For example, a glass or plastic substrate coated with a transparent conductive oxide semiconductor film such as fluorine-doped or antimony-doped tin oxide (NESA), tin-doped indium oxide (ITO), and aluminum-doped zinc oxide. Preferably, glass coated with a fluorine-doped tin oxide film is used.

A semiconductor film electrode according to the present invention is preferably made from compound semiconductor nanoparticles, and has a nanoporous structure.

Examples of the compound semiconductor material encompass: metal or composite oxides, such as $TiO_2$, $ZnO$, $In_2O_3$, $SnO_2$, $ZrO_2$, $Ta_2O_5$, $Nb_2O_5$, $Fe_2O_3$, $Ga_2O_3$, $WO_3$, and $SrTiO_3$; metal halides, such as $AgI$, $AgBr$, $CuI$, and $CuBr$; further, metal sulfides, such as $ZnS$, $TiS_2$, $ZnO$, $In_2S_3$, $SnS$, $SnS_2$, $ZrS_2$, $Ag_2S$, $PbS$, $CdS$, $TaS_2$, $CuS$, $Cu_2S$, $WS_2$, $MoS_2$, and $CuInS_2$; and metal selenides and metal tellurides, such as $CdSe$, $TiSe_2$, $ZrSe_2$, $Bi_2Se_3$, $In_2Se_3$, $SnSe$, $SnSe_2$, $Ag_2Se$, $TaSe_2$, $CuSe$, $Cu_2Se$, $WSe_2$, $MoSe_2$, $CuInSe_2$, $CdTe$, $TiTe_2$, $ZrTe_2$, $Bi_2Te_3$, $In_2Te_3$, $SnTe$, $SnTe_2$, $Ag_2Te$, $TaTe_2$, $CuTe$, $Cu_2Te$, $WTe_2$, and $MoTe_2$. However, the material is not limited to these. Preferably, an oxide semiconductor material, such as $TiO_2$, $ZnO$, and $SnO_2$ is used.

For example, titanium oxide particles may be a commercially-available particles such as P25 (produced by Degussa Japan. Co. Ltd., or NIPPON AEROSIL CO. LTD.), ST-01 (produced by ISHIHARA SANGYO KAISHYA LTD.), and SP-210 (produced by SHOWA DENKO K.K.), or crystalline titanium oxide particles obtained such that titanium alkoxide, or the like, is hydrolyzed and autoclaved, for example, by a sol-gel method, as described in J. Am. Ceram. Soc., 80, 3157 (1997). Preferably, the titanium oxide particles obtained from the titanium alkoxide by the sol-gel method is used.

Semiconductor nanoparticles forming the semiconductor film have a particle diameter of 5 nm to 1000 nm, preferably 10 nm to 300 nm.

A method for forming the semiconductor film electrode employing the oxide semiconductor may be, but not limited to, a method described below, for example. The oxide semiconductor nanoparticles are sufficiently mixed with water, a polymer (such as a polyethylene glycol), a surfactant, and the like, so as to be slurry. Then, the slurry is coated on a substrate by a method called doctor blade method. It is also possible to mix the nanoparticles with a polymer acting as a binder, and a highly-adhesive organic solvent, and then, coat it on a substrate by a screen printing method. The substrate coated with the oxide semiconductor is calcined in the atmosphere or oxygen at a temperature of 450 C.° to 500 C.° so that the oxide semiconductor film electrode can be obtained.

The semiconductor film electrode usually has a thickness of 0.5 μm to 100 μm, preferably 5 μm to 20 μm.

An adsorption of the organic dye sensitizer on a surface of the semiconductor electrode is carried out by immersing the semiconductor film electrode in a dye solution, and then, leaving at rest for one hour or more at a room temperature, or for 10 minutes to one hour under a heating condition. It is preferable to leave it at rest for six hours or more at a room temperature.

A solvent used for the dye adsorption may be: alcohol solvents such as methanol, ethanol, n-propanol, isopropanol, n-butanol, and t-butanol; organic solvents, such as chloroform, acetone, acetonitrile, tetrahydrofuran, dimethylsulfoxide, dimethylformamide, benzene, toluene, xylene, chlorobenzene, and dichlorobenzene; and mixed solvents of these. It is preferable to use ethanol, chloroform, or a t-butanol-acetonitrile mixed solvent.

The dye solution usually has a dye concentration of 0.05 mM to 0.5 mM, preferably 0.2 mM to 0.3 mM.

In the dye adsorption, in order to prevent dyes on the semiconductor electrode from being associated with each other, and make an electron transfer reaction from the dye to the semiconductor efficiently take place, it is possible to (1), in the dye solution, dissolve: cholic acid derivatives such as cholic acid, deoxycholic acid, chenodeoxycholic acid, and taurochenodeoxycholic acid; sodium salt of the cholic acid derivative; a surfactant such as triton X; glucose; and the like, and (2) make them co-adsorbed with the dyes. The common adsorbent in the dye solution usually has a concentration of 1 mM to 100 mM, preferably 5 mM to 20 mM.

An electrolyte solution employed in the photoelectric conversion element and the photoelectrochemical solar cell according to the present invention, includes a redox ion pair. The redox ion pair may be, but not limited to, $I^-/I_3^-$, $Br^-/Br_2$, $Fe^{2+}/Fe^{3+}$, $Sn^{2+}/Sn^{4+}$, $Cr^{2+}/Cr^{3+}$, $V^{2+}/V^{3+}$, $S^{2-}/S_2^-$, anthraquinone, and ferrocene. In a case of an iodine redox, an electrolyte may be a mixture of iodine and: imidazolium derivatives (methylpropylimidazolium iodide, methylbutylimidazolium iodide, ethylmethylimidazolium iodide, dimethylpropylimidazolium iodide, or the like); lithium iodide; potassium iodide; or tetraalkylammonium iodide salt, each of which includes the aforementioned ions. In a case of a bromine redox, the electrolyte may be a mixture of bromine and: lithium bromide; potassium bromide; or tetraalkylammonium bromide, each of which includes the aforementioned ions. It is preferable to use the iodine redox, such as lithium iodide, tetraalkylammonium, or imidazolium derivative iodide.

The redox electrolyte usually has a concentration of 0.05M to 1M, preferably 0.1M to 0.5M.

The solvent employed for the redox electrolyte solution may be: alcohol solvents such as methanol, ethanol, and isopropanol; nitrile solvents such as acetonitrile, methoxyacetonitrile, propionitrile, and methoxypropionitrile; carbonate solvents such as ethylene carbonate, and propylene carbonate; organic solvents such as dimethylsulfoxide, dimethylformamide, tetrahydrofuran, nitromethane, and n-methylpyrrolidone; or mixed solvents of these. Preferably, the nitrile solvent, such as acetonitrile, is used.

For an improvement in photoelectric conversion characteristics, the redox electrolyte solution employed in the photoelectric conversion element and the photoelectrochemical solar cell according to the present invention may be added with basic additives, for example, a pyridine derivative such as t-butylpyridine, as described in J. Am. Chem. Soc., 115, 6382 (1993), and the like. In this case, the electrolyte solution usually has an additive concentration of 0.05M to 1M, preferably 0.1M to 0.5M.

In place of the redox electrolyte solution employing the solvent, it is possible to use a mixture of an iodide of an imidazolium derivative, and iodine, which iodide is ambient temperature molten salt (an ionic liquid) of: 1-ethyl-3-methylimidazolium iodide, 1-n-propyl-3-methylimidazolium iodide, 1-n-butyl-3-methylimidazolium iodide, 1-n-hexyl-3-methylimidazolium iodide, or the like, each of which includes no solvent (for example, see Chem. Commun., 374 (2002), J. Phys. Chem. B, 107, 4374 (2003)).

In a case where the ambient temperature molten salt electrolyte solution is employed, it is possible to solidify the electrode by use of various gelling agents electrolyte, which gelling agents are employed in Chem. Commun., 374 (2002) and the like.

In place of the redox electrolyte solution employed in the photoelectric conversion element and the photoelectrochemical solar cell according to the present invention, it is possible to use: an inorganic p-type semiconductor hole transferable material (such as CuI, CuBr, and CuSCN) employed in J. Photochem. Photobiol. A: Chem., 117, 137 (1998), and the like; and an organic low molecular or organic high molecular hole transferable material, such as a spiropyran derivative (Nature, 395, 583 (1998)), a polypyrrole derivative (Sol. Energy Mater. Sol. Cells, 55, 113 (1998)), and a polythiophene.

A counter electrode employed in the photoelectric conversion element and the photoelectrochemical solar cell according to the present invention may be, but not limited to, a precious metal (such as Pt, Rh, and Ru) coated in a form of a film on a transparent conductive oxide-coated glass substrate, a carbon, an oxide semiconductor, or an organic macromolecular material. It is preferable to use a Pt electrode or a carbon electrode.

A spacer employed in the photoelectric conversion element and the photoelectrochemical solar cell according to the present invention is a polymer film of: polyethylene; polypropylene; ethylene vinyl acetate; or heat or light plastic resin, and usually has a thickness of 15 μm to 120 μm, preferably 15 μm to 30 μm.

EXAMPLE

Next, the present invention is described with respect to examples. Compounds of Chemical Formulas (32) to (67) are specifically showed later.

Example 1

Synthesis of Compound No. (5)

An ether solution of 10 ml (containing a 2-bromo-3-hexylthiophene of 903 mg) was dripped to magnesium of 93 mg. On completion of the dripping, a reaction solution was heated to reflux, so that a grignard reagent was prepared. The reaction solution was cooled down to a room temperature, and [1,3-Bis (diphenylphosphino) propane] nickelchloride of 19 mg was added thereto. An ether solution of 20 ml, containing a 3-iodo-9-ethylcarbazole (represented by Chemical Formula (32)) of 1.12 g, was dripped into the reaction solution, and the reaction solution was agitated for one hour at a room temperature. After that, an ammonium chloride solution was added thereto, and an extraction was carried out with ether. An organic phase thus obtained was washed with water and saturated saline, and dried with magnesium sulfate. Then, the solvent was distilled away therefrom under reduced pressure, so that a crude product was obtained. This crude product was purified by column chromatography (solvent: hexane), so that a carbazole derivative of 930 mg, which was a desired product represented by Chemical Formula (33), was obtained. An yield of the product was 74%.

$^1$H NMR data of the compound represented by Chemical Formula (33) is as follows: $^1$H NMR data (300 MHz, CDCl$_3$): δ8.14 (1H, d, J=1.5 Hz), 8.10 (1H, d, J=7.7 Hz), 7.54 (1H, dd, J=8.3, 1.5 Hz), 7.50-7.41 (3H, m), 7.27-7.25 (1H, m), 7.23 (1H, d, J=5.2 Hz), 7.01 (1H, d, J=5.2 Hz), 4.40 (2H, q, J=7.2 Hz), 2.71 (2H, dd, J=8.2, 7.4 Hz), 1.67-1.63 (2H, m), 1.47 (3H, t, J=7.2 Hz), 1.35-1.26 (6H, m), 0.84 (3H, t, J=6.8 Hz).

A tetrahydrofuran solution of 50 mL, containing the carbazole derivative (represented by Chemical Formula (33)) of 900 mg, was cooled down to a temperature of 0 C.°, and then N-bromosuccinimide of 487 mg was added thereto. After that, the mixture was agitated for 30 minutes at a room temperature. A 10% sodium carbonate aqueous solution of 30 mL was added thereto so that a reaction was stopped. An extraction was carried out with ethyl acetate, and an organic phase thus obtained was washed with water and saturated saline, and dried with magnesium sulfate. Then, the solvent was distilled away therefrom under reduced pressure, so that a crude product was obtained. This crude product was roughly purified by the column chromatography (solvent: hexane), and then, further purified by liquid chromatography. Thereby, a carbazole derivative (represented by Chemical Formula (34)) of 773 mg was obtained, to which carbazole derivative a bromine atom was introduced. An yield of the product was 70%.

$^1$H NMR data of the compound represented by Chemical Formula (34) is as follows: $^1$H NMR data (300 MHz, CDCl$_3$): δ8.09 (1H, d, J=7.7 Hz), 8.08 (1H, s), 7.53-7.40 (4H, m), 7.25 (1H, ddd, J=7.7, 6.8, 1.1 Hz), 6.96 (1H, s), 4.39 (2H, q, J=7.1 Hz), 2.63 (2H, t, J=7.7 Hz), 1.65-1.55 (2H, m), 1.47 (3H, t, J=7.1 Hz), 1.35-1.24 (6H, m), 0.84 (3H, t, J=6.8 Hz).

The carbazole derivative (represented by Chemical Formula (34)) of 366 mg and 3-hexylthiophene-2-boronic ester derivative (represented by Chemical Formula (35)) were mixed together, and heated to reflux for 24 hours in dimethoxyethane in the presence of tetrakis (triphenylphosphine) palladium of 48 mg and 2 mol/L sodium carbonate aqueous solution of 1 mL. After being cooled down to a room temperature, the mixture was diluted with ethyl acetate. Then, an organic phase thus obtained was washed with water and saturated saline, and dried with magnesium sulfate. After that, the solvent was distilled away therefrom under reduced pressure, so that a crude product was obtained. The crude product was roughly purified by the column chromatography (solvent: hexane/dichloromethane=10/1), and then, further purified by the liquid chromatography. Thereby, a carbazole derivative (represented by Chemical Formula (36)) of 349 g was obtained. An yield of the product was 80%.

$^1$H NMR data of the compound represented by Chemical Formula (36) is as follows: $^1$H NMR data (300 MHz, CDCl$_3$): δ8.17 (1H, d, J=1.1 Hz), 8.12 (1H, d, J=7.7 Hz), 7.56 (1H, dd, J=8.4, 1.8 Hz), 7.53-7.42 (3H, m), 7.29-7.23 (1H, m), 7.09 (1H, s), 7.04 (1H, d, J=1.3 Hz), 6.80 (1H, br s), 4.40 (2H, q, J=7.1 Hz), 2.70 (2H, t, J=7.8 Hz), 2.60 (2H, t, J=7.8 Hz), 1.73-1.60 (4H, m), 1.48 (3H, t, J=7.1 Hz), 1.40-1.24 (12H, m), 0.91 (3H, t, J=6.6 Hz), 0.86 (3H, t, J=6.6 Hz).

By repeating the bromination reaction described in Paragraph (0047) and the Suzuki coupling reaction described in Paragraph (0048), it becomes possible to synthesize: a carbazole derivative (represented by Chemical Formula (37)) in which three hexyl-substituted thiophene rings were fused; a carbazole derivative (represented by Chemical Formula (38)) in which four hexyl-substituted thiophene rings were fused, a carbazole derivative (represented by Chemical Formula (39)) in which five hexyl-substituted thiophene rings were fused; and a carbazole derivative (represented by Chemical Formula (40)) in which six hexyl-substituted thiophene rings were fused.

$^1$H NMR data of the compound represented by Chemical Formula (37) is as follows: $^1$H NMR data (300 MHz, CDCl$_3$): δ8.17 (1H, d, J=1.1 Hz), 8.12 (1H, d, J=7.7 Hz), 7.56 (1H, dd, J=8.4, 1.8 Hz), 7.53-7.42 (3H, m), 7.29-7.23 (1H, m), 7.09 (1H, s), 7.01 (1H, s), 6.98 (1H, br s), 6.89 (1H, br s), 4.40 (2H, q, J=7.1 Hz), 2.77-2.67 (4H, m), 2.62 (2H, t, J=7.8 Hz), 1.74-1.61 (6H, m), 1.48 (3H, t, J=7.1 Hz), 1.40-1.24 (18H, m), 0.94-0.82 (9H, m).

$^1$H NMR data of the compound represented by Chemical Formula (38) is as follows: $^1$H NMR data (300 MHz, CDCl$_3$): δ8.19 (1H, s), 8.13 (1H, d, J=7.7 Hz), 7.57 (1H, d, J=8.2 Hz), 7.54-7.43 (3H, m), 7.30-7.25 (1H, m), 7.12 (1H, s), 7.04 (1H, s), 7.00 (1H, br s), 6.99 (1H, s), 6.92 (1H, br s), 4.41 (2H, q, J=7.1 Hz), 2.83-2.69 (6H, m), 2.64 (2H, t, J=7.7 Hz), 1.78-1.62 (8H, m), 1.49 (3H, t, J=7.1 Hz), 1.48-1.26 (24H, m), 0.95-0.85 (12H, m).

$^1$H NMR data of the compound represented by Chemical Formula (39) is as follows: $^1$H NMR data (400 MHz, THF-d$_8$): δ8.18 (1H, br s), 8.12 (1H, d, J=7.9 Hz), 7.60-7.51 (3H, m), 7.44 (1H, br t, J=8.0 Hz), 7.19 (1H, br t, J=7.8 Hz), 7.17 (1H, s), 7.11 (1H, s), 7.06 (1H, s), 7.04-7.03 (3H, m), 4.47 (2H, q, J=7.2 Hz), 2.85-2.76 (4H, m), 2.73 (2H, t, J=7.7 Hz), 2.66-2.58 (4H, m), 1.73-1.60 (10H, m), 1.43 (3H, t, J=7.0 Hz), 1.42-1.25 (30H, m), 0.94-0.82 (15H, m).

$^1$H NMR data of the compound represented by Chemical Formula (40) is as follows: $^1$H NMR data (400 MHz, THF-d$_8$): δ8.19 (1H, br s), 8.12 (1H, d, J=7.8 Hz), 7.60-7.51 (3H, m), 7.44 (1H, ddd, J=8.0, 7.0, 1.0 Hz), 7.19 (1H, br t, J=7.4 Hz), 7.18 (1H, s), 7.12 (1H, s), 7.064 (1H, s), 7.061 (1H, s), 7.05 (1H, s), 7.03 (2H, m), 4.47 (2H, q, J=7.1 Hz), 2.87-2.76 (8H, m), 2.73 (2H, t, J=7.7 Hz), 2.63 (2H, t, J=7.7 Hz), 1.77-1.64 (12H, m), 1.43 (3H, t, J=7.1 Hz), 1.40-1.26 (36H, m), 0.95-0.89 (15H, m), 0.85 (3H, t, J=6.9 Hz).

A phosphorous oxychloride of 0.1 mL was dripped into N,N-dimethylformamide (hereinafter, referred to as DMF) of 1 mL under a cooled condition at a temperature of 0 C.°, and then, agitated for one hour at a room temperature. Thereby, a Vilsmeier reagent was prepared. The Vilsmeier reagent was dripped into a DMF solution of 5 mL having the carbazole derivative (represented by Chemical Formula (37)) of 224 mg at a room temperature, and then, agitated for four hours at a temperature of 70 C.°, in which carbazole derivative three hexyl-substituted thiophene rings were fused. After that, the mixture was added with a 10% sodium acetate solution of 30 mL so as to be neutralized, and an extraction was carried out with ethyl acetate. An organic phase thus obtained was washed with water and saturated saline, and dried with magnesium sulfate. Then, the solvent was distilled away therefrom under reduced pressure, so that a crude product was obtained. The crude product was roughly purified by the column chromatography (solvent: hexane/ethyl acetate=15/1), and then, further purified by the liquid chromatography. Thereby, the aldehyde derivative (represented by Chemical Formula (41)) of 195 mg was obtained. An yield of the product was 84%.

$^1$H NMR data of the compound represented by Chemical Formula (41) is as follows: $^1$H NMR data (300 MHz, CDCl$_3$): δ 10.02 (1H, s), 8.17 (1H, d, J=1.4 Hz), 8.12 (1H, d, J=7.7 Hz), 7.55 (1H, dd, J=8.5, 1.7 Hz), 7.53-7.42 (3H, m), 7.29-7.23 (1H, m), 7.14 (1H, s), 7.05 (2H, br s), 4.40 (2H, q, J=7.1 Hz), 2.95 (2H, t, J=7.7 Hz), 2.82 (2H, t, J=7.7 Hz), 2.71 (2H, t, J=7.7 Hz), 1.74-1.61 (6H, m), 1.48 (3H, t, J=7.1 Hz), 1.44-1.24 (18H, m), 0.94-0.83 (9H, m).

The aldehyde derivative (represented by Chemical Formula (41)) of 181 mg and cyanoacetic acid of 32 mg were heated to reflux for four hours in acetonitrile in the presence of piperidine of 1 mL. Then, chloroform of 20 mL was added to a reaction solution, and an organic phase thus obtained was washed with dilute hydrochloric acid, water, and saturated saline, and dried with sodium sulfate. After that, the solvent was distilled away therefrom under reduced pressure, so that a crude product was obtained. The crude product was purified by the column chromatography (first, chloroform, then ethyl acetate, after that, chloroform/ethanol=10/1), so that a dye compound (represented by Chemical Formula (5)) of 137 mg was obtained. An yield of the product was 69%.

$^1$H NMR data of the dye compound represented by Chemical Formula (5) is as follows: $^1$H NMR data (300 MHz, DMSO-d$_6$): δ 8.23-8.16 (3H, m), 7.65 (1H, d, J=8.8 Hz), 7.62 (1H, d, J=8.5 Hz), 7.51-7.44 (2H, m), 7.32 (1H, s), 7.25 (1H, s), 7.23 (1H, s), 7.19 (1H, d, J=7.4 Hz), 4.45 (2H, q, J=7.1 Hz), 2.80-2.70 (4H, m), 2.64 (2H, t, J=7.7 Hz), 1.68-1.52 (6H, m), 1.32 (3H, t, J=7.7 Hz), 1.38-1.14 (18H, m), 0.83 (3H+3H, t, J=6.6 Hz), 0.75 (3H, t, J=6.6 Hz).

Example 2

Synthesis of Compound No. (6)

A phosphorous oxychloride of 0.1 mL was dripped into a DMF of 1 mL under a cooled condition at a temperature of 0 C.°, and then, agitated for one hour at a room temperature. Thereby, a Vilsmeier reagent was synthesized. The Vilsmeier reagent was dripped into a DMF solution of 5 mL containing a carbazole derivative (represented by Chemical Formula (38)) of 270 mg at a room temperature, and then, agitated for four hours at a temperature of 70 C.°, in which carbazole derivative four hexyl-substituted thiophene rings were fused. After that, the mixture was added with a 10% sodium acetate solution of 30 mL so as to be neutralized, and an extraction was carried out with ethyl acetate. An organic phase thus obtained was washed with water and saturated saline, and dried with magnesium sulfate. Then, the solvent was distilled away therefrom under reduced pressure, so that a crude product was obtained. The crude product was roughly purified by column chromatography (solvent: hexane/ethyl acetate=20/1), and then, further purified by liquid chromatography.

Thereby, an aldehyde derivative (represented by Chemical Formula (42)) of 225 mg was obtained. An yield of the product was 81%.

$^1$H NMR data of the compound represented by Chemical Formula (42) is as follows: $^1$H NMR data (300 MHz, CDCl$_3$): δ 10.03 (1H, s), 8.18 (1H, d, J=1.4 Hz), 8.13 (1H, d, J=7.7 Hz), 7.56 (1H, dd, J=8.5, 1.7 Hz), 7.54-7.43 (3H, m), 7.30-7.24 (1H, m), 7.13 (1H, s), 7.06 (1H, s), 7.04 (1H, s), 7.01 (1H, s), 4.40 (2H, q, J=7.1 Hz), 2.96 (2H, t, J=7.7 Hz), 2.84 (2H, t, J=7.7 Hz), 2.80 (2H, t, J=7.7 Hz), 2.72 (2H, t, J=7.7 Hz), 1.77-1.64 (8H, m), 1.48 (3H, t, J=7.1 Hz), 1.44-1.26 (24H, m), 0.96-0.84 (12H, m).

The aldehyde derivative (represented by Chemical Formula (42)) of 211 mg, and cyanoacetic acid of 40 mg were heated to reflux for four hours in a mixed solvent of acetonitrile of 2 mL and toluene of 1 mL in the presence of piperidine of 1 mL. Then, chloroform of 20 mL was added to a reaction solution, and an organic phase thus obtained was washed with dilute hydrochloric acid, water, and saturated saline, and dried with sodium sulfate. After that, the solvent was distilled away therefrom under reduced pressure, so that a crude product was obtained. The crude product was purified by the column chromatography (first, chloroform, and then, ethyl acetate, after that, chloroform/ethanol=10/1, finally chloroform/ethanol=3/1), and a dye compound (represented by Chemical Formula (6)) of 216 mg was obtained. An yield of the product was 95%.

$^1$H NMR data of the dye compound represented by Chemical Formula (6) is as follows: $^1$H NMR data (300 MHz, THF-d$_8$): δ 8.39 (1H, s), 8.16 (1H, s), 8.08 (1H, d, J=7.7 Hz), 7.56-7.39 (4H, m), 7.17 (1H, d, J=7.7 Hz), 7.14 (1H, s), 7.05 (2H, s), 6.59 (1H, s), 4.42 (2H, q, J=6.9 Hz), 2.86-2.66 (8H, m), 1.71-1.60 (8H, m), 1.40 (3H, t, J=6.9 Hz), 1.40-1.25 (24H, m), 0.95-0.82 (12H, m).

Example 3

Synthesis of Compound No. (7)

A phosphorous oxychloride of 0.1 mL was dripped into a DMF of 1 mL under a cooled condition at a temperature of 0 C.°, and agitated for one hour at a room temperature. Thereby, a Vilsmeier reagent was synthesized. The Vilsmeier reagent was dripped into a DMF solution of 3 mL containing the carbazole derivative (represented by Chemical Formula (39)) of 181 mg at a room temperature, and then, agitated for four hours at a temperature of 70 C.°, in which carbazole derivative five hexyl-substituted thiophene rings were fused. After that, the mixture was added with a 10% sodium acetate solution of 30 mL so as to be neutralized, and an extraction was carried out with ethyl acetate. An organic phase thus obtained was washed with water and saturated saline, and dried with magnesium sulfate. Then, the solvent was distilled away therefrom under reduced pressure, and a crude product was obtained. The crude product was roughly purified by column chromatography (solvent: hexane/ethyl acetate=20/1), and then, further purified by liquid chromatography. Thereby, an aldehyde derivative (represented by Chemical Formula (43)) of 159 mg was obtained. An yield of the product was 84%.

$^1$H NMR data of the compound represented by Chemical Formula (43) is as follows: $^1$H NMR data (400 MHz, CDCl$_3$): δ 10.02 (1H, s), 8.16 (1H, d, J=1.1 Hz), 8.12 (1H, d, J=7.4 Hz), 7.56 (1H, dd, J=8.5, 1.7 Hz), 7.50 (1H, br t, J=7.7 Hz), 7.45 (1H, d, J=8.5 Hz), 7.44 (1H, br d, J=7.7 Hz), 7.26 (1H, m), 7.10 (1H, s), 7.05 (1H, s), 7.02 (1H, s), 7.00 (1H, s), 6.99 (1H, s), 4.41 (2H, q, J=7.1 Hz), 2.95 (2H, t, J=7.7 Hz), 2.85-2.76 (6H, m), 2.70 (2H, t, J=7.7 Hz), 1.76-1.66 (10H, m), 1.48 (3H, t, J=7.1 Hz), 1.44-1.24 (30H, m), 0.94-0.88 (12H, m), 0.85 (3H, t, J=7.1 Hz).

The aldehyde derivative (represented by Chemical Formula (43)) of 148 mg, and cyanoacetic acid of 24 mg were heated to reflux for four hours in a mixed solvent of acetonitrile of 2 mL and toluene of 1 mL in the presence of piperidine of 1 mL. Then, chloroform of 20 mL was added to a reaction solution, and an organic phase thus obtained was washed with dilute hydrochloric acid, water, and saturated saline, and dried with sodium sulfate. After that, the solvent was distilled away therefrom under reduced pressure, so that a crude product was obtained. The crude product was purified by the column chromatography (first, chloroform, and then, ethyl acetate, after that, chloroform/ethanol=10/1, finally, chloroform/ethanol=4/1), so that a dye compound (represented by Chemical Formula (7)) of 43 mg was obtained. An yield of the product was 27%.

$^1$H NMR data of the dye compound represented by Chemical Formula (7) is as follows: $^1$H NMR data (300 MHz, THF-d$_8$): δ 8.41 (1H, s), 8.18 (1H, s), 8.12 (1H, d, J=7.7 Hz), 7.62-7.50 (4H, m), 7.45-7.40 (1H, m), 7.24 (1H, d, J=3.4 Hz), 7.25-7.05 (4H, m), 4.47 (2H, q, J=7.2 Hz), 2.99-2.80 (6H, m), 2.73 (2H, t, J=7.8 Hz), 1.72-1.55 (5H, m), 1.54-1.25 (30H, m), 0.99-0.75 (12H, m).

Example 4

Synthesis of Compound No. (8)

A phosphorous oxychloride of 0.1 mL was dripped into a DMF of 1 mL under a cooled condition at temperature of 0 C.°, and agitated for one hour at a room temperature. Thereby, a Vilsmeier reagent was synthesized. The Vilsmeier reagent was dripped into a DMF solution of 4 mL containing a carbazole derivative (represented by Chemical Formula (40)) of 253 mg at a room temperature, and then, agitated for four hours at a temperature of 70 C.°, in which carbazole ring six hexyl-substituted thiophene rings were fused. After that, the mixture was added with a 10% sodium acetate solution of 30 mL so as to be neutralized, and an extraction was carried out with ethyl acetate. An organic phase thus obtained was washed with water and saturated saline, and dried with magnesium sulfate. Then, the solvent was distilled away therefrom under reduced pressure, so that a crude product was obtained. The crude product was roughly purified by column chromatography (solvent: hexane/ethyl acetate=10/1), and further purified by liquid chromatography. Thereby, an aldehyde derivative (represented by Chemical Formula (44)) of 97 mg was obtained. An yield of the product was 38%.

$^1$H NMR data of the compound represented by Chemical Formula (44) is as follows: $^1$H NMR data (400 MHz, THF-d$_8$): δ 10.03 (1H, s), 8.18 (1H, d, J=1.0 Hz), 8.12 (1H, d, J=7.7 Hz), 7.60-7.51 (3H, m), 7.44 (1H, ddd, J=8.2, 7.0, 1.1 Hz), 7.19 (1H, ddd, J=8.0, 7.0, 1.0 Hz), 7.19 (1H, s), 7.18 (1H, s), 7.12 (2H, s), 7.09 (1H, s), 7.07 (1H, s), 4.47 (2H, q, J=7.1 Hz), 3.00 (2H, t, J=7.8 Hz), 2.90-2.81 (8H, m), 2.73 (2H, t, J=7.8 Hz), 1.77-1.66 (12H, m), 1.44 (3H, t, J=7.1 Hz), 1.42-1.26 (36H, m), 0.94-0.88 (12H, m), 0.85 (3H, t, J=7.0 Hz).

The aldehyde derivative (represented by Chemical Formula (44)) of 88 mg and cyanoacetic acid of 12 mg were heated to reflux for four hours in a mixed solvent of acetonitrile of 2 mL and toluene of 1 mL in the presence of piperidine of 0.5 mL. After that, chloroform of 20 mL was added to a reaction solution, and an organic phase thus obtained was washed with dilute hydrochloric acid, water, and saturated saline, and dried with sodium sulfate. Then, the solvent was distilled away therefrom under reduced pressure, so that a crude product was obtained. The crude product was purified by the column chromatography (first, chloroform, and then, ethyl acetate, after that, chloroform/ethanol=10/1, finally chloroform/ethanol=4/1), so that a dye compound (represented by Chemical Formula (8)) of 91 mg was obtained. An yield of the product was 99%.

$^1$H NMR data of the dye compound represented by Chemical Formula (8) is as follows: $^1$H NMR data (400 MHz, THF-d$_8$): δ 8.41 (1H, s), 8.19 (1H, br s), 8.11 (1H, d, J=7.7 Hz), 7.60-7.50 (3H, m), 7.43 (1H, ddd, J=8.2, 7.2, 1.0 Hz), 7.25 (1H, s), 7.19 (1H, br t, J=7.2 Hz), 7.18 (1H, s), 7.13 (1H, s), 7.12 (1H, s), 7.09 (1H, s), 7.07 (1H, s), 4.46 (2H, q, J=7.1 Hz), 2.91 (2H, t, J=7.7 Hz), 2.89-2.80 (8H, m), 2.73 (2H, t, J=7.7 Hz), 1.77-1.64 (12H, m), 1.43 (3H, t, J=7.1 Hz), 1.46-1.26 (36H, m), 0.96-0.88 (15H, m), 0.85 (3H, t, J=7.0 Hz).

Example 5

Synthesis of Compound No. (9)

9-ethylcarbazole-3-boronic ester (represented by Chemical Formula (45)) of 130 mg, and a monobromo-quarter-thiophene derivative (represented by Chemical Formula (46)) of 183 mg were mixed together, and heated to reflux for 24 hours in dimethoxyethane in the presence of tetrakis (triphenylphosphine) palladium of 37 mg, and a 2 mol/L sodium carbonate aqueous solution of 1 mL. The mixture was cooled down to a room temperature, and diluted with ethyl acetate. Then, an organic phase thus obtained was washed with water and saturated saline, and dried with magnesium sulfate. After that, the solvent was distilled away therefrom under reduced pressure, so that a crude product was obtained. The crude product was roughly purified by column chromatography (solvent: hexane/ethyl acetate=50/1), and further purified by liquid chromatography (solvent: hexane/ethyl acetate=50/1). Thereby, a carbazole derivative (represented by Chemical Formula (47)) of 197 mg was obtained. An yield of the product was 90%.

$^1$H NMR data of the compound represented by Chemical Formula (47) is as follows: $^1$H NMR data (300 MHz, CDCl$_3$): δ 8.35 (1H, d, J=1.7 Hz), 8.18 (1H, br d, J=7.7 Hz), 7.75 (1H, dd, J=8.5, 1.7 Hz), 7.52 (1H, ddd, J=8.2, 7.1, 1.1 Hz), 7.43 (1H, d, J=8.5 Hz), 7.39 (1H, d, J=8.5 Hz), 7.33 (1H, dd, J=5.2, 1.1 Hz), 7.31 (1H, d, J=3.8 Hz), 7.29 (1H, m), 7.18 (1H, dd, J=3.6, 1.1 Hz), 7.16 (1H, d, J=3.8 Hz), 7.10 (1H, dd, J=5.2, 3.6 Hz), 7.058 (1H, s), 7.055 (1H, s), 4.36 (2H, q, J=7.1 Hz), 2.85 (2H, t, J=7.7 Hz), 2.78 (2H, t, J=7.7 Hz), 1.81-1.65 (4H, m), 1.46 (3H, t, J=7.1 Hz), 1.42-1.31 (12H, m), 0.96 (3H, t, J=6.7 Hz), 0.95 (3H, t, J=6.7 Hz).

Formylation of the carbazole derivative represented by Chemical Formula (47) was carried out by the Vilsmeier reaction as carried out in Paragraph (0050). The reaction was taken place with the use of the carbazole derivative (47) of 117 mg, and a crude product thus obtained was roughly purified by the column chromatography (solvent: hexane/ethyl acetate=7/1), and further purified by the liquid chromatography (solvent: hexane/ethyl acetate=5/1). Thereby, an aldehyde derivative (represented by Chemical Formula (48)) of 80 mg was obtained. An yield of the product was 66%.

$^1$H NMR data of the compound represented by Chemical Formula (48) is as follows: $^1$H NMR data (400 MHz, CDCl$_3$): δ 9.88 (1H, s), 8.32 (1H, d, J=1.7 Hz), 8.15 (1H, d, J=7.7 Hz), 7.74 (1H, dd, J=8.5, 1.7 Hz), 7.70 (1H, d, J=4.0 Hz), 7.50 (1H, ddd, J=8.2, 7.1, 1.0 Hz), 7.42 (1H, d, J=8.2 Hz), 7.41 (1H, d, J=8.5 Hz), 7.30 (1H, d, J=3.6 Hz), 7.27 (1H, br t, J=7.4 Hz), 7.22 (1H, d, J=4.0 Hz), 7.14 (1H, d, J=3.6 Hz), 7.07 (1H, s), 7.04 (1H, s), 4.39 (2H, q, J=7.2 Hz), 2.83 (2H, t, J=7.8 Hz), 2.76 (2H, t, J=7.8 Hz), 1.76-1.66 (4H, m), 1.46 (3H, t, J=7.2 Hz), 1.43-1.30 (12H, m), 0.92 (3H, t, J=6.7 Hz), 0.90 (3H, t, J=6.7 Hz).

The aldehyde derivative (represented by Chemical Formula (48)) of 60 mg and cyanoacetic acid of 14 mg were heated to reflux for four hours in acetonitrile in the presence of piperidine of 1 mL. Then, a reaction solution was purified without any modifications by the column chromatography (first, chloroform, and then, chloroform/ethanol=10/1, after that, chloroform/ethanol=5/1), so that a dye compound (represented by Chemical Formula (9)) of 40 mg was obtained. An yield of the product was 61%.

$^1$H NMR data of the compound represented by Chemical Formula (9) is as follows: $^1$H NMR data (400 MHz, THF-d$_8$): δ 8.40 (1H, br s), 8.31 (1H, s), 8.07 (1H, d, J=7.6 Hz), 7.64 (1H, d, J=7.9 Hz), 7.58 (1H br s), 7.46-7.37 (2H, m), 7.35 (1H, d, J=7.1 Hz), 7.29 (1H, br s), 7.18-7.08 (3H, m), 7.05 (1H, br s), 7.00 (1H, br s), 4.31 (2H, q, J=7.1 Hz), 2.82-2.68 (4H, m), 1.78-1.63 (4H, m), 1.50-1.28 (15H, m), 0.91 (3H, t, J=6.9 Hz), 0.88 (3H, t, J=6.9 Hz).

Example 6

Synthesis of Compound No. (10)

9-ethylcarbazole-3-boronic ester (represented by Chemical Formula (45)) of 180 mg, and a monobromo-quarter-thiophene derivative (represented by Chemical Formula (49)) of 226 mg were mixed together, and heated to reflux for 24 hours in dimethoxyethane in the presence of tetrakis (triphenylphosphine) palladium of 27 mg, and a 2 mol/L sodium carbonate aqueous solution of 1 mL. The mixture was cooled down to a room temperature, and diluted with ethyl acetate. Then, an organic phase thus obtained was washed with water and saturated saline, and dried with magnesium sulfate. After that, the solvent was distilled away therefrom under reduced pressure, so that a crude product was obtained. The crude product was roughly purified by column chromatography (solvent: hexane/ethyl acetate=50/1), and further purified by liquid chromatography (solvent: hexane/ethyl acetate=20/1). Thereby, a carbazole derivative (represented by Chemical Formula (50)) of 166 mg was obtained. An yield of the product was 61%.

$^1$H NMR data of the compound represented by Chemical Formula (50) is as follows: $^1$H NMR data (300 MHz, CDCl$_3$): δ 8.32 (1H, br s), 8.15 (1H, br d, J=7.7 Hz), 7.72 (1H, br d, J=8.0 Hz), 7.50 (1H, br dd, J=8.0, 7.1 Hz), 7.42 (1H, br d, J=7.7 Hz), 7.40 (1H, d, J=8.0 Hz), 7.26 (1H, br dd, J=8.0, 7.1 Hz), 7.21-7.15 (4H, m), 7.09 (1H, br s), 7.04 (1H, d, J=3.9 Hz), 6.95 (1H, d, J=5.2 Hz)), 4.39 (2H, q, J=7.1 Hz), 2.83-2.77 (4H, m), 1.81-1.61 (4H, m), 1.46 (3H, t, J=7.1 Hz), 1.41-1.29 (12H, m), 0.93 (3H, t, J=6.7 Hz), 0.91 (3H, t, J=6.7 Hz).

Formylation of the carbazole derivative represented by Chemical Formula (50) was carried out by the Vilsmeier reaction as carried out in Paragraph (0048). The reaction was carried out with the use of the carbazole derivative (represented by Chemical Formula (50)) of 384 mg, and a crude product thus obtained was roughly purified by the column chromatography (solvent: hexane/ethyl acetate=7/1), and further purified by the liquid chromatography (solvent: hexane/ethyl acetate=5/1). Thereby, an aldehyde derivative (represented by Chemical Formula (51)) of 179 mg was obtained. An yield of the product was 45%.

$^1$H NMR data of the compound represented by Chemical Formula (51) is as follows: $^1$H NMR data (300 MHz, CDCl$_3$):

δ 9.80 (1H, s), 8.31 (1H, br s), 8.14 (1H, d, J=7.7 Hz), 7.56 (1H, s), 7.49 (1H, br dd, J=8.0, 7.1 Hz), 7.41 (1H, d, J=8.0 Hz), 7.38 (1H, d, J=8.5 Hz), 7.27 (1H, br dd, J=8.0, 7.1 Hz), 7.21-7.14 (4H, m), 7.08 (1H, d, J=3.6 Hz), 4.35 (2H, q, J=7.1 Hz), 2.83 (2H, t, J=7.7 Hz), 2.81 (2H, t, J=7.7 Hz), 1.81-1.63 (4H, m), 1.44 (3H, t, J=7.1 Hz), 1.42-1.24 (12H, m), 0.95-0.87 (6H, m).

The aldehyde derivative (represented by Chemical Formula (51)) of 180 mg, and cyanoacetic acid of 43 mg were heated to reflux for four hours in a mixed solvent of acetonitrile of 2 mL and toluene of 1 mL in the presence of piperidine of 1 mL. Then, chloroform of 20 mL was added to a reaction solution, and an organic phase thus obtained was washed with dilute hydrochloric acid, water, and saturated saline, and dried with sodium sulfate. After that, the solvent was distilled away therefrom under reduced pressure, so that a crude product was obtained. The crude product was purified by the column chromatography (first, chloroform, and then, chloroform/ethanol=9/1), so that a dye compound (represented by Chemical Formula (10)) of 185 mg was obtained. An yield of the product was 94%.

$^1$H NMR data of the dye compound represented by Chemical Formula (10) is as follows: $^1$H NMR data (400 MHz, DMSO-$d_8$): δ 8.46 (1H, s), 8.23 (1H, d, J=7.7 Hz), 8.15 (1H, s), 7.70 (1H, dd, J=8.5, 1.8 Hz), 7.63 (1H, s), 7.60 (1H, d, J=8.5 Hz), 7.58 (1H, d, J=8.5 Hz), 7.46 (1H, ddd, J=8.1, 7.1, 1.0 Hz), 7.45 (1H, s), 7.37, (1H, d, J=4.0 Hz), 7.36 (1H, d, J=4.0 Hz), 7.27 (1H, d, J=4.0 Hz), 7.22 (1H, br t, J=7.6 Hz), 7.15 (1H, s), 4.41 (2H, q, J=7.1 Hz), 2.76 (2H, t, J=7.7 Hz), 2.73 (2H, t, J=7.7 Hz), 1.72-1.55 (4H, m), 1.42-1.21 (12H, m), 1.30 (3H, t, J=7.1 Hz), 0.87-0.82 (6H, m).

Example 7

Synthesis of Compound No. (11)

The carbazole derivative (represented by Chemical Formula (52)) of 336 mg, and commercially-available bithiophene boronic ester of 243 mg were mixed together, and heated to reflux for 24 hours in dimethoxyethane in the presence of tetrakis (triphenylphosphine) palladium of 65 mg, and a 2 mol/L sodium carbonate aqueous solution of 1 mL. After being cooled down to a room temperature, the mixture was diluted with ethyl acetate. Then, an organic phase thus obtained was washed with water and saturated saline, and dried with magnesium sulfate. After that, the solvent was distilled away therefrom under reduced pressure, so that a crude product was obtained. The crude product was roughly purified by column chromatography (solvent: hexane/ethyl acetate=50/1), and further purified by liquid chromatography (solvent: hexane/ethyl acetate=25/1). Thereby, a carbazole derivative (represented by Chemical Formula (54)) of 365 mg was obtained. An yield of the product was 95%.

$^1$H NMR data of the compound represented by Chemical Formula (54) is as follows: $^1$H NMR data (300 MHz, CDCl$_3$): δ 8.17 (1H, br s), 8.13 (1H, d, J=7.7 Hz), 7.56 (1H, dd, J=8.5, 1.7 Hz), 7.54-7.43 (3H, m), 7.29-7.19 (4H, m), 7.14 (1H, d, J=3.9 Hz), 7.10 (1H, s), 7.05 (1H, d, J=3.9 Hz), 7.03 (1H, s), 4.41 (2H, q, J=7.1 Hz), 2.78 (2H, t, J=7.7 Hz), 2.70 (2H, t, J=7.7 Hz), 1.76-1.63 (4H, m), 1.48 (3H, t, J=7.1 Hz), 1.44-1.24 (12H, m), 0.91 (3H, t, J=6.7 Hz), 0.86 (3H, t, J=6.7 Hz).

Formylation of the carbazole derivative represented by Chemical Formula (54) was carried out by the Vilsmeier reaction as carried out in Paragraph (0050). The reaction was taken place with the use of the carbazole derivative (54) of 416 mg, and a crude product thus obtained was roughly purified by the column chromatography (solvent: hexane/ ethyl acetate=10/1), and further purified by the liquid chromatography (solvent: hexane/ethyl acetate=6/1). Thereby, an aldehyde derivative (represented by Chemical Formula (55)) of 280 mg was obtained. An yield of the product was 65%.

$^1$H NMR data of the compound represented by Chemical Formula (55) is as follows: $^1$H NMR data (300 MHz, CDCl$_3$): δ 9.86 (1H, s), 8.17 (1H, br s), 8.12 (1H, d, J=7.7 Hz), 7.66 (1H, d, J=3.8 Hz), 7.54-7.43 (3H, m), 7.32 (1H, d, J=3.8 Hz), 7.29-7.23 (2H, m), 7.12 (1H, s), 7.09 (1H, d, J=3.8 Hz), 7.04 (1H, s), 4.40 (2H, q, J=7.1 Hz), 2.78 (2H, t, J=7.7 Hz), 2.71 (2H, t, J=7.7 Hz), 1.76-1.63 (4H, m), 1.48 (3H, t, J=7.1 Hz), 1.44-1.24 (12H, m), 0.92 (3H, t, J=6.6 Hz), 0.86 (3H, t, J=6.6 Hz).

The aldehyde derivative (represented by Chemical Formula (55)) of 250 mg, and cyanoacetic acid of 59 mg were heated to reflux for four hours in a mixed solvent of acetonitrile of 2 mL and toluene of 1 mL in the presence of piperidine of 1 mL. Then, chloroform of 20 mL was added to a reaction solution, and an organic phase thus obtained was washed with dilute hydrochloric acid, water, and saturated saline, and dried with sodium sulfate. After that, the solvent was distilled away therefrom under reduced pressure, so that a crude product was obtained. The crude product was purified by the column chromatography (first, chloroform, and then, ethyl acetate, after that, chloroform/ethanol=5/1, finally, chloroform/ethanol=1/1), so that a dye compound (represented by Chemical Formula (11)) of 132 mg was obtained. An yield of the product was 48%.

$^1$H NMR data of the dye compound represented by Chemical Formula (11) is as follows: $^1$H NMR data (400 MHz, THF-$d_8$): δ 8.35 (1H, s), 8.13 (1H, s), 8.11 (1H, d, J=7.6 Hz), 7.77 (1H, br s), 7.54-7.49 (3H, m), 7.46 (1H, br s), 7.43 (1H, ddd, J=8.0, 7.0, 1.0 Hz), 7.37 (1H, br s), 7.21-7.16 (3H, m), 7.13 (1H, s), 4.45 (2H, q, J=7.1 Hz), 2.72 (2H, t, J=7.7 Hz), 2.72 (2H, t, J=7.7 Hz), 1.76-1.65 (4H, m), 1.42 (3H, t, J=7.1 Hz), 1.39-1.25 (12H, m), 0.91 (3H, t, J=6.9 Hz), 0.84 (3H, t, J=6.9 Hz).

Example 8

Synthesis of Compound No. (12)

A carbazole derivative represented by Chemical Formula (57) can be synthesized by carrying out the bromination reaction described in Paragraph (0047) and the Suzuki coupling reaction described in Paragraph (0048) twice independently with the use of the carbazole derivative represented by Chemical Formula (56).

$^1$H NMR data of the compound represented by Chemical Formula (57) is as follows: $^1$H NMR data (300 MHz, CDCl$_3$): δ 8.32 (1H, d, J=1.4 Hz), 8.15 (1H, d, J=7.7 Hz), 7.73 (1H, br d, J=8.2 Hz), 7.50 (1H, t, J=7.7 Hz), 7.42 (1H, d, J=7.0 Hz), 7.39 (1H, d, J=8.0 Hz), 7.30-7.25 (2H, m), 7.17 (1H, d, J=3.6 Hz), 7.10 (1H, d, J=3.8 Hz), 7.07 (1H, d, J=3.8 Hz), 7.01 (1H, s), 6.98 (1H, br s), 6.91 (1H, br s), 4.37 (2H, q, J=7.1 Hz), 2.75 (2H, t, J=7.7 Hz), 2.62 (2H, t, J=7.7 Hz), 1.73-1.60 (4H, m), 1.45 (3H, t, J=7.1 Hz), 1.44-1.26 (12H, m), 0.94-0.89 (6H, m).

Formylation of the carbazole derivative represented by Chemical Formula (57) was carried out by the Vilsmeier reaction as carried out in Paragraph (0050). The reaction was taken place with the use of the carbazole derivative (57) of 250 mg, and a crude product thus obtained was roughly purified by column chromatography (solvent: hexane/ethyl acetate=10/1), and further purified by liquid chromatography (solvent: hexane/ethyl acetate=5/1). Thereby, an aldehyde derivative (represented by Chemical Formula (58)) of 165 mg was obtained. An yield of the product was 63%.

¹H NMR data of the compound represented by Chemical Formula (58) is as follows: ¹H NMR data (400 MHz, CDCl₃): δ 10.01 (1H, s), 8.32 (1H, d, J=1.7 Hz), 8.15 (1H, d, J=7.6 Hz), 7.73 (1H, dd, J=8.5, 1.7 Hz), 7.50 (1H, ddd, J=8.2, 7.0, 1.1 Hz), 7.43 (1H, d, J=8.2 Hz), 7.42 (1H, d, J=8.5 Hz), 7.28 (1H, d, J=3.8 Hz), 7.27 (1H, br t, J=7.4 Hz), 7.19 (1H, d, J=3.8 Hz), 7.13 (2H, s), 7.04 (2H, s), 4.40 (2H, q, J=7.1 Hz), 2.95 (2H, t, J=7.8 Hz), 2.81 (2H, t, J=7.8 Hz), 1.75-1.66 (4H, m), 1.46 (3H, t, J=7.1 Hz), 1.42-1.30 (12H, m), 0.91 (3H, t, J=7.0 Hz), 0.90 (3H, t, J=7.0 Hz).

The aldehyde derivative (represented by Chemical Formula (58)) of 165 mg, and cyanoacetic acid of 39 mg were heated to reflux for four hours in a mixed solvent of acetonitrile of 2 mL and toluene of 1 mL in the presence of piperidine of 1 mL. Then, chloroform of 20 mL was added to a reaction solution, and an organic phase thus obtained was washed with dilute hydrochloric acid, water, and saturated saline, and dried with sodium sulfate. After that, the solvent was distilled away therefrom under reduced pressure, so that a crude product was obtained. The crude product was purified by the column chromatography (first, chloroform, and then, chloroform/ethanol=10/1, after that, chloroform/ethanol=5/1), so that a dye compound (represented by Chemical Formula (12)) of 120 mg was obtained. An yield of the product was 67%.

¹H NMR data of the dye compound represented by Chemical Formula (12) is as follows: ¹H NMR data (400 MHz, DMSO-d₆): δ 8.47 (1H, d, J=1.6 Hz), 8.23 (1H, d, J=7.6 Hz), 8.14 (1H, s), 7.74 (1H, dd, J=8.7, 1.5 Hz), 7.62-7.60 (2H, m), 7.50 (1H, dd, J=3.8 Hz), 7.47 (1H, ddd, J=8.2, 7.0, 1.2 Hz), 7.36 (1H, d, J=3.8 Hz), 7.34 (1H, d, J=3.8 Hz), 7.29 (1H, d, J=3.8 Hz), 7.28 (1H, s), 7.22 (1H, br t, J=7.4 Hz), 7.19 (1H, s), 4.43 (2H, q, J=7.1 Hz), 2.76 (2H, br t, J=7.6 Hz), 2.72 (2H, br t, J=7.6 Hz), 1.68-1.52 (4H, m), 1.30 (3H, t, J=7.1 Hz), 1.37-1.21 (12H, m), 0.85 (3H, t, J=7.0 Hz), 0.84 (3H, t, J=7.0 Hz).

Example 9

Synthesis of Compound No. (15)

A tetrahydrofuran solution (represented by Chemical Formula (59)) of 4 mL was dripped to magnesium of 204 mg, the tetrahydrofuran solution containing 4-hexyloxybromobenzene of 1.8 g. On completion of the dripping, a reaction solution was heated to reflux, so that a grignard reagent was prepared. In the presence of [1,3-bis(diphenylphosphino) propane] nickelchloride of 50 mg, the prepared grignard reagent was dripped into a tetrahydrofuran solution (represented by Chemical Formula (32)) of 10 mL, the tetrahydrofuran solution containing 3-iode-9-ethylcarbazole of 1.0 g, and being cooled down to a temperature of 0 C.°. After the dripping, a reaction solution was heated to reflux for one night. Then, the reaction solution was raised to a room temperature, and an ammonium chloride solution was added thereto. Thereby, the reaction was stopped. An extraction was carried out with ethyl acetate. An organic phase thus obtained was washed with water and saturated saline, and dried with magnesium sulfate. Then, the solvent was distilled away therefrom, so that a crude product was obtained. The crude product was purified by the column chromatography (solvent: hexane), so that a carbazole derivative (represented by Chemical Formula (60)) of 471 mg was obtained, which carbazole derivative was the desired product. An yield of the product was 40%.

¹H NMR data of the compound represented by Chemical Formula (60) is as follows: ¹H NMR data (300 MHz, CDCl₃): δ8.28 (1H, d, J=1.6 Hz), 8.15 (1H, d, J=7.8 Hz), 7.66 (1H, dd, J=6.7, 1.8 Hz), 7.64 (2H, d, J=8.7 Hz), 7.52-7.40 (1H, m), 7.45 (2H, d, J=8.4 Hz), 7.25 (1H, t, J=7.3 Hz), 7.02 (2H, d, J=8.7 Hz), 4.40 (2H, q, J=7.2 Hz), 4.03 (2H, t, J=6.6 Hz), 1.90-1.78 (2H, m), 1.55-1.34 (9H, m), 0.94 (3H, t, J=7.0 Hz).

By repeating the bromination reaction described in Paragraph (0047), and the Suzuki coupling reaction described in Paragraph (0048) with the use of the carbazole derivative (represented by Chemical Formula (60)), it is possible to synthesis a carbazole derivative (represented by Chemical Formula (61)) in which three hexyl-substituted thiophene rings are fused, and another carbazole derivative (represented by Chemical Formula (62)) in which four hexyl-substituted thiophene rings are fused.

¹H NMR data of the compound represented by Chemical Formula (61) is as follows: ¹H NMR data (300 MHz, CDCl₃): δ 8.36 (1H, d, J=1.2 Hz), 8.32 (1H, d, J=1.0 Hz), 7.74 (1H, dd, J=8.6, 1.7 Hz), 7.70 (1H, dd, J=8.7, 1.8 Hz), 7.67 (2H, d, J=8.9 Hz), 7.43 (1H, d, J=8.6), 7.39 (1H, d, J=8.6), 7.22 (1H, s), 7.04 (2H, d, J=8.7 Hz), 7.02 (1H, s), 6.93 (1H, s), 4.36 (2H, q, J=7.2 Hz), 4.05 (2H, t, J=6.6 Hz), 2.83 (4H, m), 2.65 (2H, t, J=7.6 Hz), 1.92-1.60 (8H, m), 1.60-1.28 (27H, m), 1.0-0.87 (12H, m). s ¹H NMR data of the compound represented by Chemical Formula (62) is as follows: ¹H NMR data (300 MHz, CDCl₃): δ 8.37 (1H, d, J=1.4 Hz), 8.32 (1H, d, J=1.4 Hz), 7.74 (1H, dd, J=8.5, 1.7 Hz), 7.70 (1H, dd, J=8.6, 1.6 Hz), 7.66 (2H, d, J=8.7 Hz), 7.43 (1H, d, J=8.5 Hz), 7.39 (1H, d, J=8.6 Hz), 7.23 (1H, s), 7.04 (1H, s), 7.03 (2H, d, J=8.7 Hz), 7.04-6.99 (2H, m), 6.29 (1H, s), 4.37 (2H, q, J=7.2 Hz), 4.04 (2H, t, J=6.6 Hz), 2.91-2.75 (6H, m), 2.64 (2H, t, J=7.7 Hz), 1.92-1.63 (9H, m), 1.58-1.26 (34H, m), 1.00-0.85 (15H, m).

Formylation of the carbazole derivative represented by Chemical Formula (61) was carried out by the Vilsmeier reaction as carried out in Paragraph (0050). The reaction was taken place with the use of the carbazole derivative (61) of 208 mg, and a crude product thus obtained was roughly purified by the column chromatography (solvent: hexane/ ethyl acetate=20/1), and further purified by the liquid chromatography (solvent: hexane/ethyl acetate=15/1). Thereby, an aldehyde derivative (represented by Chemical Formula (63)) of 140 mg was obtained. An yield of the product was 68%.

¹H NMR data of the compound represented by Chemical Formula (63) is as follows: ¹H NMR data (300 MHz, CDCl₃): δ10.0 (1H, s), 8.35 (1H, d, J=1.6 Hz), 8.30 (1H, d, J=1.6 Hz), 7.74 (1H, dd, J=8.5, 1.7 Hz), 7.68 (1H, dd, J=8.4, 1.6 Hz), 7.64 (2H, d, J=8.6 Hz), 7.45 (1H, d, J=8.5 Hz), 7.40 (1H, d, J=8.6 Hz), 7.22 (1H, s), 7.05 (1H, s), 7.03 (1H, s), 7.02 (2H, d, J=8.8 Hz), 4.39 (2H, q, J=7.2 Hz), 4.03 (2H, t, J=6.6 Hz), 2.95 (2H, t, J=7.7 Hz), 2.84 (4H, t, J=7.8 Hz), 1.89-1.66 (8H, m), 1.55-1.27 (27H, m), 0.98-0.85 (12H, m).

The aldehyde derivative (represented by Chemical Formula (63)) of 120 mg, and cyanoacetic acid of 22 mg were heated to reflux for four hours in a mixed solvent of acetonitrile of 1 mL and toluene of 0.5 mL in the presence of the piperidine of 0.2 mL. Then, a reaction solution was purified without any modifications by the column chromatography (first, chloroform, and then, ethyl acetate, after that, chloroform/ethanol=10/1, finally, chloroform/ethanol=1/1), so that a dye compound (represented by Chemical Formula (15)) of 50 mg was obtained. An yield of the product was 40%.

¹H NMR data of the dye compound represented by Chemical Formula (15) is as follows: ¹H NMR data (300 MHz, CDCl₃): δ8.47 (1H, s), 8.41 (1H, s), 8.40 (1H, s), 7.74 (1H, d, J=8.4 Hz), 7.70 (1H, d, J=8.6 Hz), 7.65 (2H, d, J=8.7 Hz), 7.53 (1H, d, J=4.8 Hz), 7.51 (1H, d, J=4.8 Hz), 7.36 (1H, s), 7.23 (1H, s), 7.13 (1H, s), 6.99 (2H, d, J=8.8 Hz), 4.45 (2H, q, J=7.1 Hz), 4.01 (2H, t, J=6.5 Hz), 2.95-2.82 (6H, m), 1.85-1.63 (8H, m), 1.58-1.28 (27H, m), 0.98-0.87 (12H, m).

Example 10

Synthesis of Compound No. (16)

Formylation of the carbazole derivative represented by Chemical Formula (62) was carried out by the Vilsmeier reaction as carried out in Paragraph (0049). The reaction was taken place with the use of the carbazole derivative (62) of 178 mg, and a crude product thus obtained was roughly purified by the column chromatography (solvent: hexane/ethyl acetate=20/1), and further purified by the liquid chromatography (solvent: hexane/ethyl acetate=15/1). Thereby, an aldehyde derivative (represented by Chemical Formula (64)) of 154 mg was obtained. An yield of the product was 85%.

$^1$H NMR data of the compound represented by Chemical Formula (64) is as follows: $^1$H NMR data (300 MHz, CDCl$_3$): δ 10.0 (1H, s), 8.35 (1H, br s), 8.30 (1H, br s), 7.74-7.65 (2H, m), 7.64 (2H, d, J=8.5 Hz), 7.44 (1H, d, J=8.6 Hz), 7.39 (1H, d, J=8.6 Hz), 7.21 (1H, s), 7.05 (1H, s), 7.02 (1H, s), 7.02 (2H, d, J=8.3 Hz), 4.38 (2H, q, J=7.2 Hz), 4.03 (2H, t, J=6.5 Hz), 2.95 (2H, t, J=7.6 Hz), 2.90-2.78 (6H, m), 1.89-1.63 (9H, m), 1.58-1.24 (34H, m), 0.98-0.85 (15H, m).

The aldehyde derivative (represented by Chemical Formula (64)) of 134 mg, and cyanoacetic acid of 22 mg were heated to reflux for four hours in a mixed solvent of acetonitrile of 1 mL and toluene of 0.5 mL in the presence of piperidine of 0.2 mL. Then, a reaction solution was purified by the column chromatography (first, chloroform, and then, ethyl acetate, after that, chloroform/ethanol=10/1, finally, chloroform/ethanol=1/1), so that a dye compound (represented by Chemical Formula (16)) of 50 mg was obtained. An yield of the product was 34%.

$^1$H NMR data of the dye compound represented by Chemical Formula (16) is as follows: $^1$H NMR data (300 MHz, CDCl$_3$): δ8.47 (1H, s), 8.41 (1H, s), 8.40 (1H, s), 7.74 (1H, d, J=8.3 Hz), 7.70 (1H, d, J=8.8 Hz), 7.65 (2H, d, J=7.9 Hz), 7.55-7.48 (2H, m), 7.35 (1H, s), 7.24 (1H, s), 7.13 (1H, s), 7.10 (1H, s), 6.99 (2H, d, J=8.2 Hz), 4.46 (2H, d, J=6.9 Hz), 4.01 (2H, t, J=6.3 Hz), 2.96-2.78 (8H, m), 1.83-1.64 (10H, m), 1.57-1.28 (33H, m), 1.00-0.85 (15H, m).

A dye compound (represented by Chemical Formula (65)) in which three unsubstituted thiophene rings are fused can be synthesized by the Suzuki coupling reaction described in Paragraph (0048), the Vilsmeier reaction described in Paragraph (0050), and a reaction with cyanoacetic acid described in Paragraph (0051), by using 3-iode-9-ethylcarbazole (represented by Chemical Formula (32)), and terthiophene boronic acid ester (represented by Chemical Formula (66)) as raw materials.

An aldehyde derivative (represented by Chemical Formula (67)) of 40 mg, and cyanoacetic acid of 14 mg were heated to reflux for four hours in an acetonitrile-chloroform mixed solvent in the presence of piperidine of 0.5 mL. Then, a reaction solution was cooled down to a room temperature. Crystals that were separated out were filtered, and purified by recrystallization with the use of a chloroform-ethanol mixture. Thereby, a dye compound (represented by Chemical Formula (65)) of 40 mg was obtained. An yield of the product was 87%.

$^1$H NMR data of the dye compound represented by Chemical Formula (65) is as follows: $^1$H NMR data (300 MHz, DMSO-d$_6$): δ 8.50 (1H, s), 8.25 (1H, d, J=7.7 Hz), 8.12 (1H, s), 7.78 (1H, dd, J=8.5, 1.7 Hz), 7.72 (1H, d, J=3.8 Hz), 7.66 (1H, d, J=8.8 Hz), 7.62 (1H, d, J=8.5 Hz), 7.53 (1H, d, J=3.8 Hz), 7.50-7.45 (3H, m), 7.44 (1H, d, J=3.8 Hz), 7.37 (1H, d, J=3.8 Hz), 7.23 (1H, t, J=7.4 Hz), 4.45 (2H, q, J=7.1 Hz), 1.32 (3H, t, J=7.1 Hz).

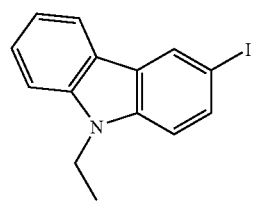

(32)

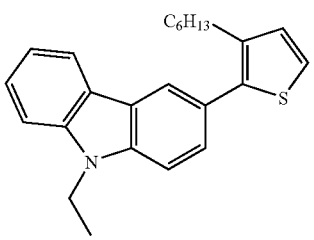

(33)

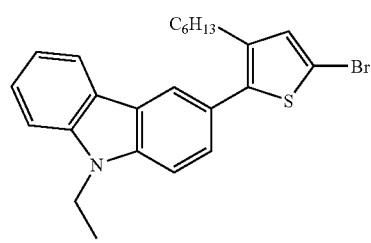

(34)

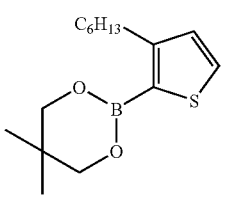

(35)

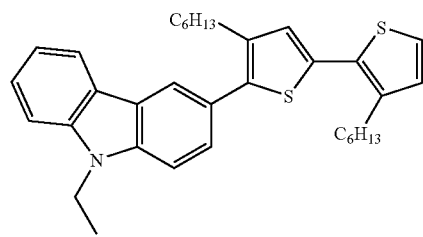

(36)

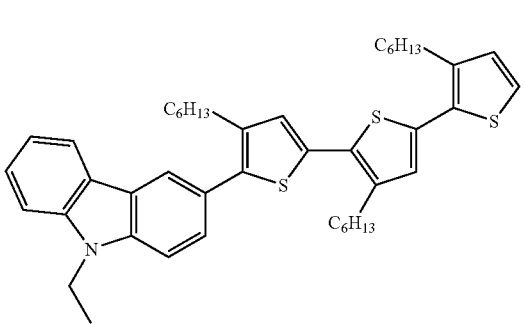

(37)

-continued
(38)
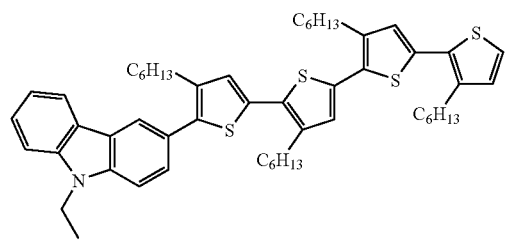
(39)
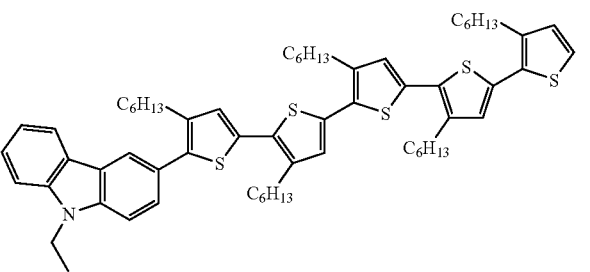
(40)
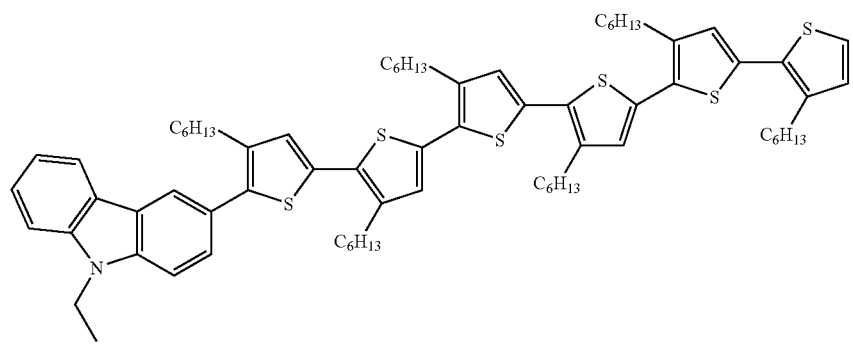
(41)
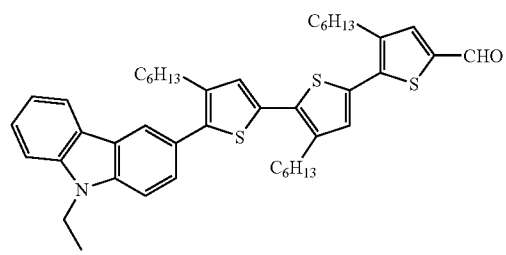
(42)
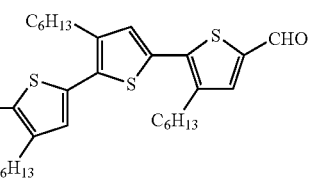
(43)
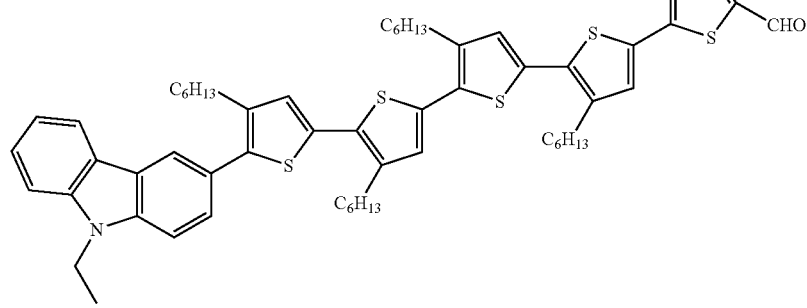
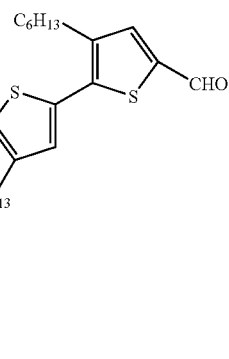
(44)
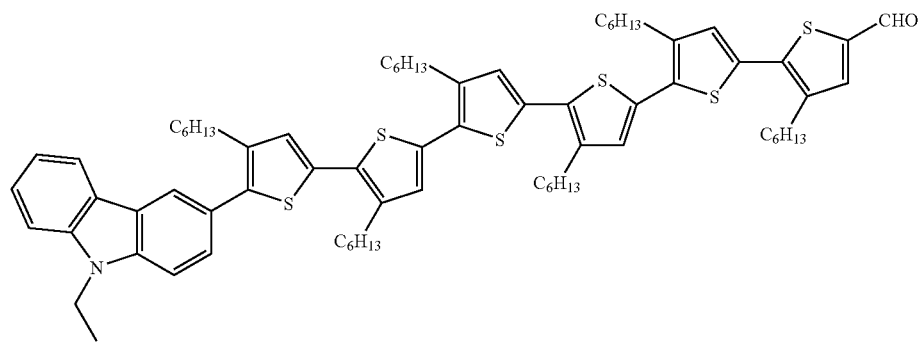

-continued
(45)
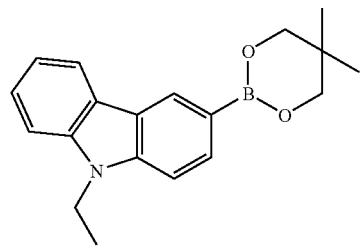
(46)
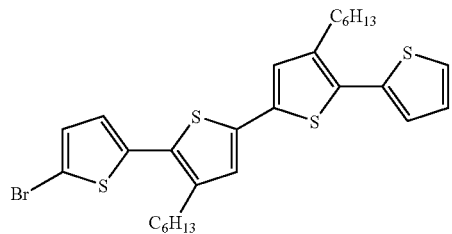
(47)
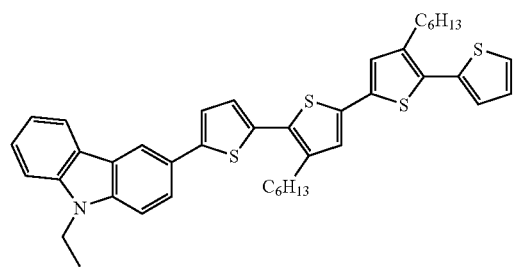
(48)
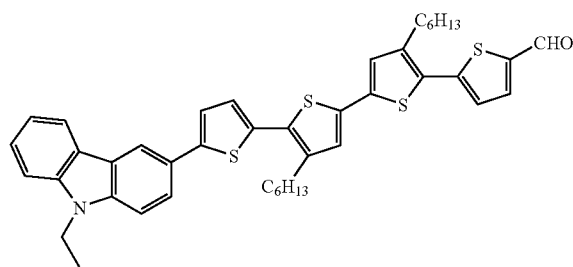
(49)
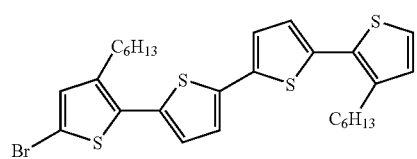
(50)
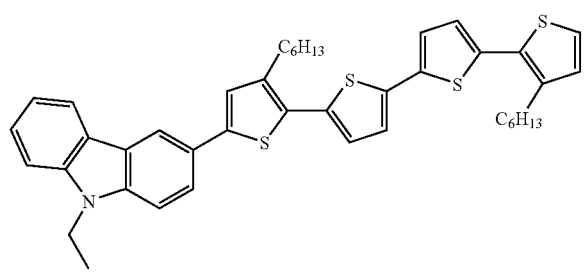
(51)
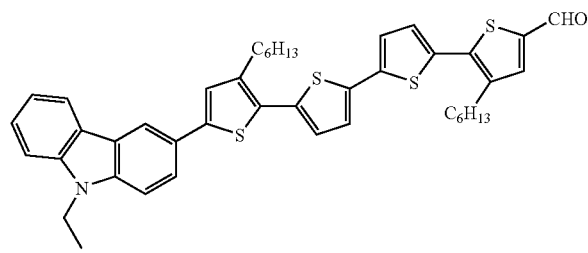
(52)
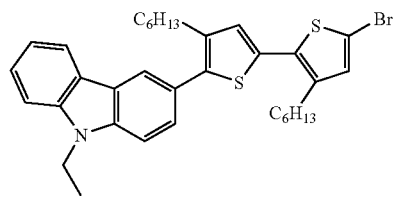
(53)
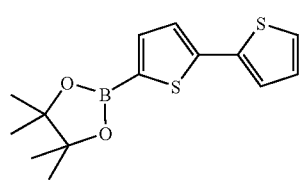
(54)
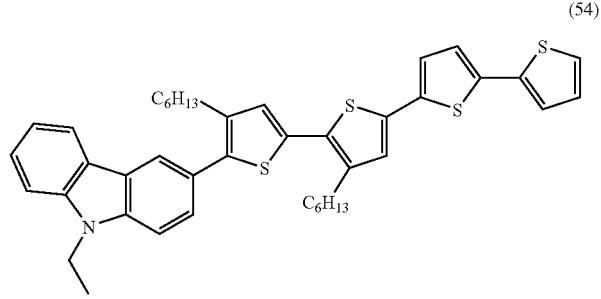
(55)
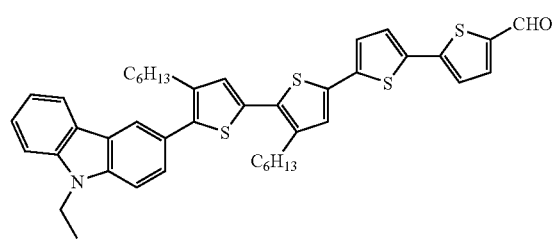
(56)
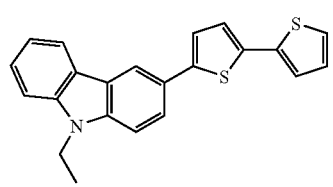

-continued
(57)
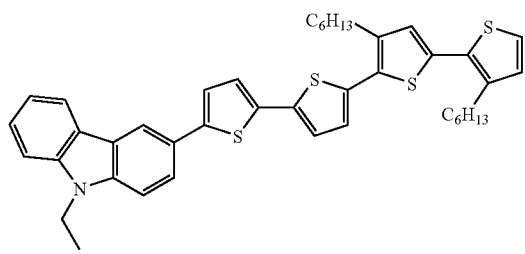
(58)
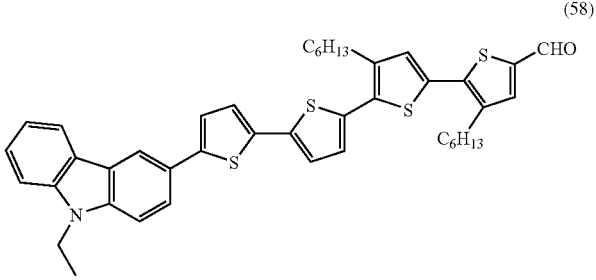
(59)
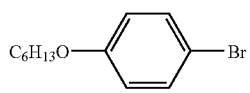
(60)
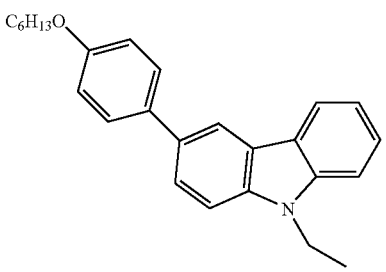
(61)
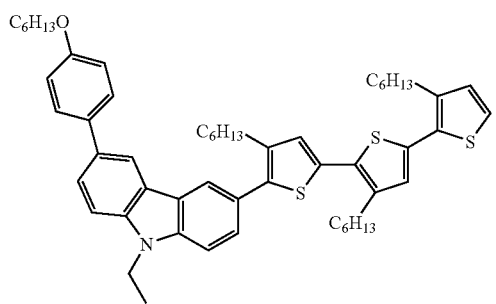
(62)
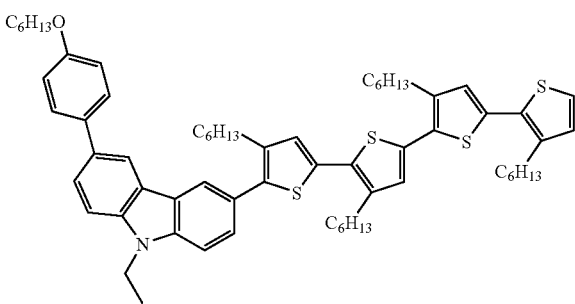
(63)
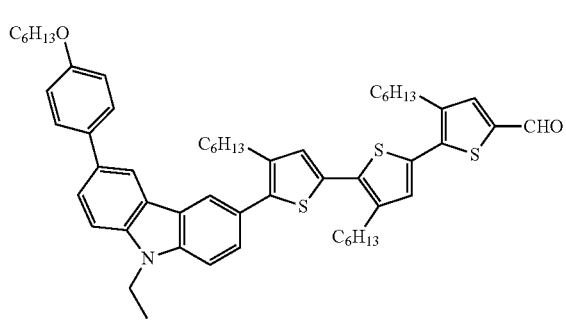
(64)
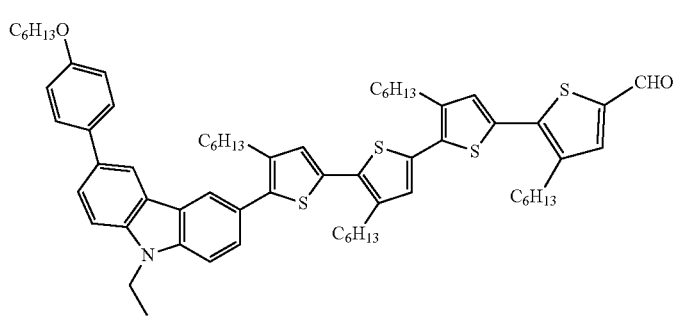

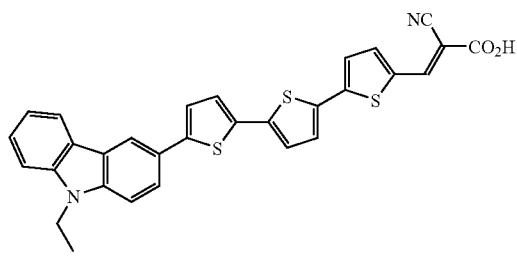

(65)

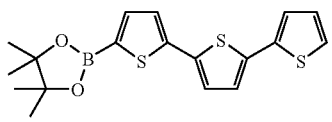

(66)

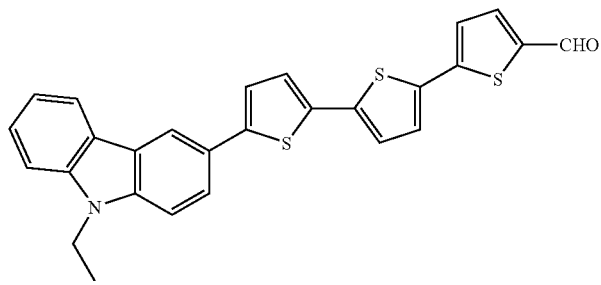

(67)

Example 11

(1) Production of Organic Dye-Adsorbed Titanium Oxide Film Electrode

Titanium oxide colloids that had been produced by hydrolyzing titanium tetraisopropoxide were autoclaved so that crystalline titanium oxide nanoparticles were obtained. The nanoparticles were mixed with ethyl cellulose as a binder, and α-terpineol as solvent, so that an organic paste was produced. This paste may be replaced by a commercially-available titanium oxide paste (produced by Solaronix Co., for example). A tin oxide-coated conductive glass was coated with the titanium oxide paste thereon by a screen printing method, and calcined for one to two hours at a temperature of 500 C.° in the atmosphere. Thereby, a titanium oxide film electrode having a thickness of 3 to 20 micron was obtained. This electrode was immersed in an organic dye solution (solvent: toluene/t-butanol/acetonitrile=1/1/1) of 0.3 mM, and left at rest for 10 hours or more at a room temperature. Thereby, an organic dye-adsorbed titanium oxide film electrode was obtained.

(2) Production of a Photoelectrochemical Solar Cell, and Evaluation of Photoelectric Conversion Characteristics The titanium oxide film electrode (having a thickness of 6 micron) produced in (1) was adsorbed with dyes showed in Table 1, and overlapped with, via a polyethylene film spacer, a counter electrode that is tin oxide-coated conductive glass sputtered with platinum. Gap between them was infused with an acetonitrile solution of 0.6M 1,2-dimethyl-3-propylimidazolium-0.1M-lithium-iodide-0.0 5M iodine-0.5M t-butylpyridine iodide, and then, immobilized with a gem clip. Thereby, a cell was produced. Photoelectric conversion characteristics of the cell were determined with a solar simulator formed from a xenon lamp as a light source, and an AM filter, and photoelectric current voltage characteristics were determined with a source meter.

TABLE 1

| | DYE | Voc/V |
|---|---|---|
| COMPERATIVE EXAMPLE | 65 | 0.63 |
| COMPERATIVE EXAMPLE | 68 | 0.60 |

TABLE 1-continued

| | DYE | Voc/V |
|---|---|---|
| COMPERATIVE EXAMPLE | 69 | 0.63 |
| COMPERATIVE EXAMPLE | 70 | 0.63 |
| COMPERATIVE EXAMPLE | 71 | 0.62 |
| PRESENT INVENTION | 5 | 0.71 |
| PRESENT INVENTION | 6 | 0.72 |
| PRESENT INVENTION | 7 | 0.70 |
| PRESENT INVENTION | 8 | 0.71 |
| PRESENT INVENTION | 9 | 0.70 |
| PRESENT INVENTION | 10 | 0.72 |
| PRESENT INVENTION | 11 | 0.72 |
| PRESENT INVENTION | 12 | 0.71 |
| PRESENT INVENTION | 15 | 0.78 |
| PRESENT INVENTION | 16 | 0.75 |
| REFERENCE EXAMPLE | 72 | 0.79 |

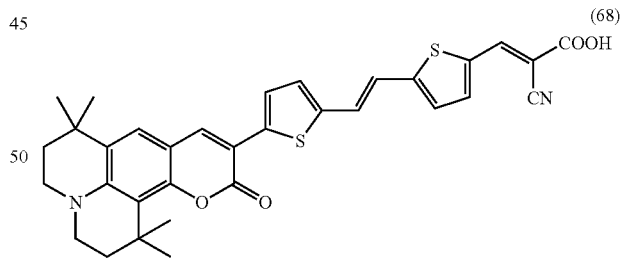

(68)

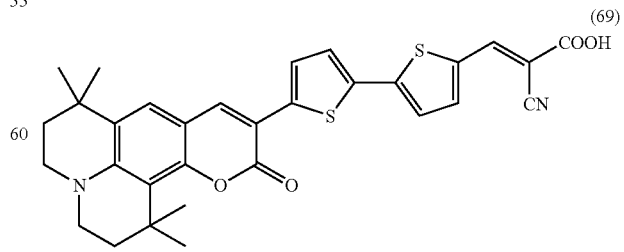

(69)

(70)

TABLE 1-continued

| DYE | Voc/V |
|---|---|

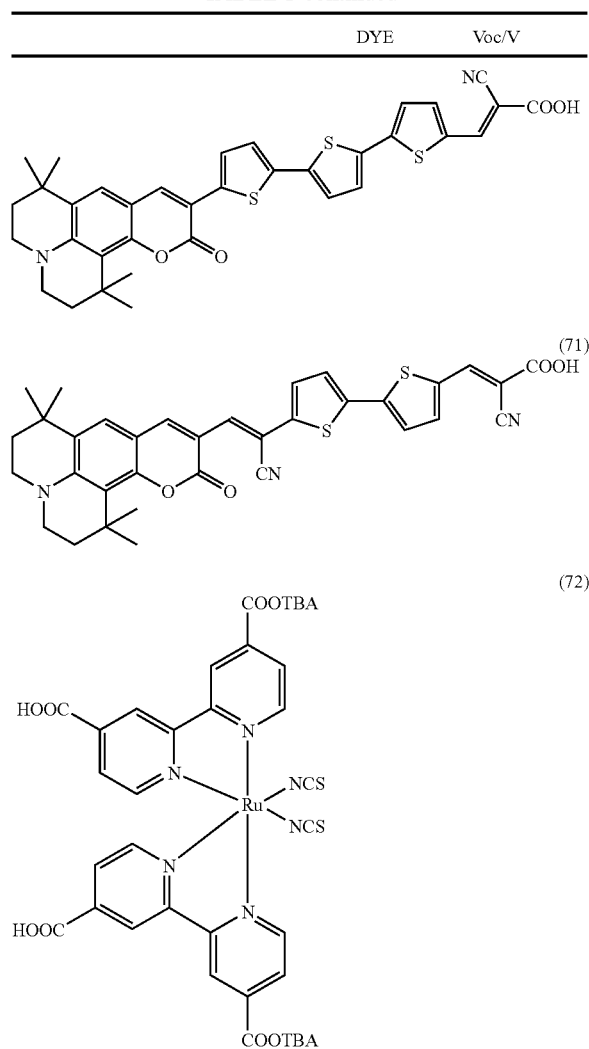

Here, TBA stands for a tetrabutyl ammonium cation.

Table 1 shows the photoelectric conversion characteristics of: photoelectrochemical solar cells (under an AM 1.5G condition) employing a carbazole organic dye synthesized according to the present invention; and, as comparative examples, a photoelectrochemical solar cell employing another carbazole organic dye (65) having no alkyl group at a thiophene linking region; and photoelectrochemical solar cells employing conventional coumarin organic dyes (68-71). Here, Jsc is a light short-circuit current density, Voc is a light open circuit voltage, Fill Factor is a form factor, and n is photoelectric conversion efficiency. As showed in Table 1, all the photoelectrochemical solar cells employing newly-developed organic dyes of the present invention successfully improved in Voc, resulting in 0.70V or more, compared with the electrochemical solar cell employing the conventional organic dyes, that is, the coumarin dyes of NKX-2700(68), NKX-2677(69), NKX-2697(70), and NKX-2883(71). Further, it was found that the photoelectrochemical solar cell employing the carbazole organic dye having no alkyl group at the thiophene linking region had a Voc of 0.63V, but the cell of the present invention had a Voc of 0.70V or more. One of the reasons of this may be considered that an alkyl chain of the dye synthesized by the present invention sterically suppressed recombination of electrons and iodine redox ions on a surface of titanium oxide. Therefore, it was demonstrated that the organic dye according to the present invention can have a Voc equal to a Voc of N719 dye (72) that was a ruthenium complex of a reference example.

(3) Evaluation of Life of Electron in Titanium Oxide

In the solar cell employing the organic dye synthesized by the present invention, the solar cell produced in (2), a life of an electron in a titanium oxide electrode was evaluated by an intensity-modulated photovoltage spectroscopy (an IMVS method such as J. Phys. Chem. B, 109, 3480 (2005), and J. Phys. Chem. B, 109, 23776 (2005), for example) employing a pump laser beam, and a potentiostat. The life of the electron in titanium oxide varies depending on an amount of electrons ionized from the dye and injected into titanium oxide, so that the comparison was made on a basis of electron life values under a condition where a Jsc value was 10 mA/cm$^2$.

TABLE 2

| | DYE | LIFE OF ELECTRON |
|---|---|---|
| COMPARATIVE EXAMPLE | 73 (NKX-2587) | 0.00053 SECONDS |
| COMPARATIVE EXAMPLE | 69 (NKX-2677) | 0.0025 SECONDS |
| COMPARATIVE EXAMPLE | 70 (NKX-2697) | 0.0012 SECONDS |
| PRESENT INVENTION | 5 (MK-1) | 0.0073 SECONDS |

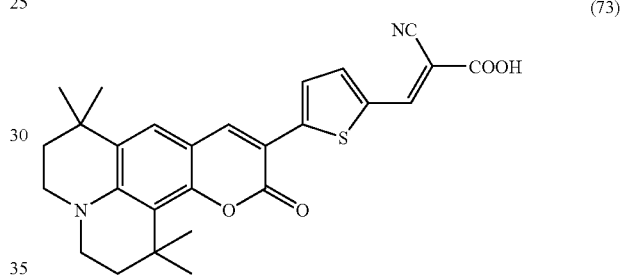

Table 2 shows the lives of the electron in the titanium oxide electrode in the solar cell employing the organic dye synthesized by the present invention. As showed in Table 2, the life of the electron successfully extends, compared with the conventional coumarin dyes of NKX-2587(73), NKX-2677(69), and NKX-2697(70). This long life of the electron shows that recombination of the electrons in titanium oxide with iodine redox ions is hardly taken place. The long life ensures an improvement in Voc. This result demonstrates the dye synthesized by the present invention improves a Voc, and efficiently raises conversion efficiency.

The invention claimed is:

1. An organic compound represented by the following general formula(1):

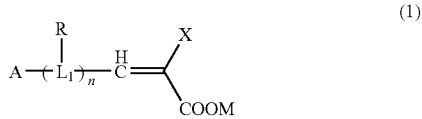

wherein A is a carbazole ring; L$_1$ is an electron transfer linking group consisting of one or more heterocyclic rings selected from the group consisting of a thiophene ring, a furan ring, a pyrrole ring, and a condensed heterocyclic ring formed from any combinations of these rings; R is a substituent group bound to at least one electron transfer linking group selected from the group consisting of an alkyl group, an alkoxy group, and an aryl group; X is at least one electron withdrawing group selected from the group consisting of a cyano group, a carboxylic acid group, an ester group, an amide group, a trifluoromethyl group, a pentafluoroethyl group, a sulfonate group, a trifluoromethanesulfonate group, and the like; M is a hydrogen atom or a salt-forming cation; and n is an integer of 1 to 12.

2. A semiconductor film electrode employing an organic compound according to claim 1 as an organic dye.

3. A photoelectric conversion element employing a semiconductor film electrode according to claim 2.

4. A photoelectrochemical solar cell employing a photoelectric conversion element according to claim 3.

* * * * *